United States Patent [19]
Duffy

[11] Patent Number: 5,871,917
[45] Date of Patent: Feb. 16, 1999

[54] IDENTIFICATION OF DIFFERENTIALLY METHYLATED AND MUTATED NUCLEIC ACIDS

[75] Inventor: Hao-peng Xu Duffy, Centerport, N.Y.

[73] Assignee: North Shore University Hospital Research Corp., Manhasset, N.Y.

[21] Appl. No.: 657,866

[22] Filed: May 31, 1996

[51] Int. Cl.[6] .......................... C07H 21/04; C07H 21/03; C12Q 1/68; C12P 19/34
[52] U.S. Cl. ........................ 435/6; 435/91.2; 536/23.1; 536/24.3; 536/24.33
[58] Field of Search ...................... 435/6, 91.2; 536/23.1, 536/24.3, 24.33

[56] References Cited

U.S. PATENT DOCUMENTS 5,436,142  7/1995  Wigler et al. .

OTHER PUBLICATIONS

Clark et al, "CpNpGp Methylation in Mammalian Cells", Nature Genetics, vol. 10, May 1995, pp. 20–27.

Little et al, "Methylation and p16; Suppressing the Suppressor", Nature Medicine, vol. 1, No. 7, Jul. 1995, pp. 633–634.

Merlo et al, "5' CpG Island Methylation is Associated with Transcriptional Silencing of the Tumour Suppressor p16/CDKN2/MTS1 in Human Cancers", Nature Medicine, vol. 1 No. 7, Jul. 1995, pp. 686–692.

Parrish et al, "Methods for Finding Genes A Major Rate–Limiting Step in Positional Cloning", GATA, vol. 10, No. 2, 1993, pp. 29–41.

Lisitsyn et al, "Cloning the Differences Between Two Complex Genomes", Science, vol. 259, Feb. 12, 1993, pp. 946–951.

Laird et al, "DNA Methylation and Cancer", Human Molecular Genetics, vol. 3, 1994, pp. 1487–1495.

Xu et al, "New Polymorphic Markers in the Vicinity of the Pearl Locus on Mouse Chromosome 13",Mammalian Genome, vol. 7, 1996, pp. 16–19.

Wieland, et al, "A Method for Difference Cloning: Gene Amplification Following Subtractive Hybridization", Proc. Natl. Acad. Sci, USA 87, 1990, pp. 2720–272.

Braun et al, "Identification of Target Genes For The Ewing's Sarcoma EWS/LFI Fusion Protein by Representational Difference Analysis", Molecular and Cellular Biology, vol. 15, No. 8, Aug. 1995, 4623–4630.

Chang, et al, "Identification of Herpesvirus–Like DNA Sequences in AIDS–Associated Kaposi's Sarcoma", Science, vol. 266, Dec. 16, 1994, pp. 1865–1869.

Hubank et al, "Identifying Differences in mRNA Expression by Representational Difference Analysis of cDNA", Nucleic Acids Research, vol. 22, No. 26, 1994, pp. 5640–5648.

(List continued on next page.)

*Primary Examiner*—W. Gary Jones
*Assistant Examiner*—Dianne Rees
*Attorney, Agent, or Firm*—Kenyon & Kenyon

[57] ABSTRACT

The present invention provides Methyl- (or Mutant-) Differential Display (MDD) methods and nucleic acid probes for detecting mutations and the methylation patterns of nucleic acids. The methods of the present invention are particularly useful for detecting and isolating genomic DNA fragments which are near coding and regulatory regions of genes and which are differentially mutated or methylated relative to the corresponding DNA from normal cells. Genes are frequently not methylated in the cells where they are expressed but are methylated in cell types where they are not expressed. Moreover, tumor cell DNA is frequently methylated to a different extent and in different regions than is the DNA of normal cells. The present invention is used for identifying which regions of the genome are methylated or mutated in different cell types, including cancerous cell types. The present invention is also used for diagnosing whether a tissue sample is cancerous, and whether that cancerous condition is non-metastatic or metastatic.

79 Claims, 11 Drawing Sheets

OTHER PUBLICATIONS

Lisitsyn et al, "Direct Isolation of Polymorphic Markers Linked to a Trait by Genetically Directed Representational Difference Analysis", Nature Genetics, vol 6, Jan. 1994, pp. 57–63.

Issa, et al, "The Estrogen Receptor CpG Island Is Methylated in Most Hematopoietic Neoplasms", Cancer Research, vol. 56, Mar. 1, 1996, pp. 973–977.

Costello et al, "Silencing of p16/CDKN2 Expression in Human Gliomas by Methylation and Chromatin Condensation", Cancer Research vol. 56, May 15, 1996, pp. 2405–2410.

Loebel et al, "Methylation Analysis of a Marsupial X–linked CpG Island by Disulfite Genomic Sequencing", Genome Research vol. 6, 1996 pp. 114–123.

Frommer et al, "A Genomic Sequencing Protocol that Yields a Positive Display of 5–Methylcytosine Residues in Individual DNA Strands", Genetics, vol. 89, Mar. 1992, pp. 1827–1831.

Horsthemke, et al, "PCR–Mediated Cloning of HpaII Tiny Fragments from Microdissected Human Chromosomes", PCR Methods and Applications, vol. 1, 1992, pp. 229–237.

McGrew et al, "Quantitation of Genomic Methylation Using Ligation Mediated PCR", BioTechniques, vol. 15, No. 4, 1993, pp. 722–724.

Singer–Sam et al, "A Quantitative HpaII–PCR Assay to Measure Methylation of DNA From a Small Number of Cells", Nucleic Acids Research, vol. 18, No. 3, Dec. 4, 1989, p. 687.

Steigerwald, et al, "Ligation–Mediated PCR Improves the Sensitivity of Methylation Analysis by Restriction Enzymes and Detection of Specific DNA Strand Breaks", Nucleic Acids Research, vol. 18, No. 6, Dec. 15, 1989, pp. 1435–1439.

Graff et al, "E–Cadherin Expression Is Silenced by DNA Hypermethylation in Human Breast and Prostate Carcinomas", Cancer Research, vol. 55, Nov. 15, 1995, pp. 5195–5199.

Belinsky, et al, "Increased Crytosine DNA–Methyltransferase Activity is Target–Cell–Specific and An Early Event in Lung Cancer", Genetics, vol. 93, Apr. 1996, pp. 4045–4050.

Willison, "Opposite Imprinting of the Mouse Igf2 and Igf2r Genes", Trends in Genetics vol. 7, 1991, pp. 107–109.

Clark et al. Nature Genetics 10: 20–27, 1995.

Fieler and Jacobs Plant Mol. Biol. 17: 321–333 (Attached Genbank Sequence Listing), 1991.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
      ( A ) LENGTH: 24 base pairs
      ( B ) TYPE: nucleic acid
      ( C ) STRANDEDNESS: both
      ( D ) TOPOLOGY: linear ( i i ) MOLECULE TYPE: cDNA ( x i ) SEQUENCE DESCRIPTION: SEQ ID NO:1:

CTCGTCGTCA GGTCAGTGCT TCAC      24

( 2 ) INFORMATION FOR SEQ ID NO:2:

( i ) SEQUENCE CHARACTERISTICS:
      ( A ) LENGTH: 12 base pairs
      ( B ) TYPE: nucleic acid
      ( C ) STRANDEDNESS: both
      ( D ) TOPOLOGY: linear ( i i ) MOLECULE TYPE: cDNA ( x i ) SEQUENCE DESCRIPTION: SEQ ID NO:2:

CGGTGAAGCA CT      12

( 2 ) INFORMATION FOR SEQ ID NO:3:

( i ) SEQUENCE CHARACTERISTICS:
    ( A ) LENGTH: 24 base pairs
    ( B ) TYPE: nucleic acid
    ( C ) STRANDEDNESS: both
    ( D ) TOPOLOGY: linear ( i i ) MOLECULE TYPE: cDNA ( x i ) SEQUENCE DESCRIPTION: SEQ ID NO:3:

TAGAGCCACG TAGCTGCTGT AGTC                                                               24

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:4:

CGGACTACAG CA                                                                            12

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:5:

ACCGTGGACT GGATAGGTTC AGAC                                                            24

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:6:

CGGTCTGAAC CT                                                                            12

( 2 ) INFORMATION FOR SEQ ID NO:7:

( i ) SEQUENCE CHARACTERISTICS:
        ( A ) LENGTH: 309 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:7:

CCGGGGCCCC ACAGGCCCCG TGCTGAAACA GGGCTGGAAC CAGGCAACTT GTTTCTTTGT     60

CCTGACATCC CTGCGCAGCT GGTACCGAGT GGACAGCCCC AACAAACTCA TGAACCCGCT    120

GGTCGCTGGG GTCTTCGGAG CCATTGTGGG AGCGGCCAGT GTCTTCGGAA ATGCTCCTCT    180

GCACGAGATC GAGCCCCAGA TGCGGGACCT GGAGGTGCAC AAATGCATAA CACATGGGAC    240

TGTGGCTGCA AATCCTGAGG GAAGGGCACA AGACCTTCCT ACAAGGGCAC TATTGCCCGC    300

CTGGGCCGG 309

( 2 ) INFORMATION FOR SEQ ID NO:8:

( i ) SEQUENCE CHARACTERISTICS:
        ( A ) LENGTH: 332 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:8:

```
CCGGGCAATC  TCCACAGGCA  CTCCTTCCAC  TGTCTGTACA  ACGTCCTTAG  CTCTTCCTTC     60
TGCCCAGTGT  GCAATCTTCC  CAGATGGGCC  TTCTGCCACA  CATTCACGTC  TGATCTGGCA    120
GGTGTTTCTT  CTGCCAAACC  TTCATCCTTC  TCGGATGCTC  TTCTGCCACA  TGTGCAATCC    180
TGTCAGACGT  TCCTGCCACT  CGAGGTAGCT  GGTCTGATGT  GAGCATGGAA  CCAGGGGGTC    240
CCCCTACCAC  CACCAGGAAT  GTCAGATGAT  CATGAGGTGT  CGGTTGGGCG  GTTCTTGAAC    300
CCTATCTATG  GAGGATAACC  GCTCACGGCC  GG                                   332
```

( 2 ) INFORMATION FOR SEQ ID NO:9:

( i ) SEQUENCE CHARACTERISTICS:
        ( A ) LENGTH: 568 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:9:

```
CCGGCCTGGG  AGGAGGGTTC  CCACCAGGCT  TTCTCAAGCC  CATCACAAGT  GAGTCAGGAA     60
CCATCTCCCA  TTGGTCCTGG  TAAGGAGGAG  ATTTGGAGGA  AGGACTGGGA  AGCCTGTGGA    120
GCGGGAGGGT  ACTGGGGGTG  GAAGTGGAAG  AAGGTGGCAC  AGTAACAGAC  TCCCTTCTCC    180
TGAGATTCCC  AGCATGGATT  GGAGGGGCTG  CCCTGCAGCG  TCCCTTACCC  CTTGTTACCT    240
GGCAGCCTGC  AAGTAGCTCT  AGGGCCAGCC  ATGTGGTCAC  CTACATCTGT  TGGGGAGAG    300
AAGGAAAACA  GATGCCCCGA  GTCGTAGAGA  CTTGCATTAT  CAGCCCTGG   GTCCAACAGC   360
AAGTGAGCTA  AGCACTTGCA  AATGTTATCT  GATGTATTCT  TTATAAGAAG  GGGTCACAAA   420
ACTGAGACTT  AGAACATGTA  AGAGGGAGAC  AGGGATTTGA  GCCTGGATCA  GCTATGTGAG   480
GATCTCCTGT  CTGTCCCCGC  TGGTTCCAAT  TCAGGTCTTA  GAGTAAAAGG  GTTGGGGATG   540
AGCTCTCTGG  CAGGACAGTG  CCCTCCGG                                         568
```

( 2 ) INFORMATION FOR SEQ ID NO:10:

( i ) SEQUENCE CHARACTERISTICS:
        ( A ) LENGTH: 1005 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:10:

```
CCGGAGGCAG  GCACAGGACT  CGGGAGGGAC  GCTGCCAGCT  CTCTGGGTGC  TGAGTTCACA     60
AGGCTGCATT  CATGATTTTC  AATAGACCTG  TGATGGTCTG  TGCCCAGTGC  TGGGACACA    120
GAAGAGTCAA  ACCTGGCTCC  TGACCTGGAC  CTGGATCATC  ACGTGACAGG  GAGGAGAGCG   180
```

-continued

| | | | | | | |
|---|---|---|---|---|---|---|
| ATCCAGGCTG | ATGAGGAAAG | CGCATGACAT | GGGGTCTTAG | GAGCAGTGAG | GGGCAGAGCC | 240 |
| ATGGCCAAAG | GCCCCGCCAT | GGAAGCTGAG | GACTCTGGCA | CCAGATGGAG | GCAGTTGACC | 300 |
| GACCTCTGCC | CTTGGGGTCC | AACCCATGGG | CTTCTCATAC | ATAGGGGTGA | AAAAGGCCAT | 360 |
| TCTATTTATG | CAGAATTTTC | CCATGTGGCC | AGGCAGCAGA | AGTCCAGAGG | GGTAGGGGCC | 420 |
| ACTCAGGGTC | ACACAGAACA | GCAGTTGCTG | AAGACTGGGG | AAGTCCAGGC | CTAGGCTCCA | 480 |
| CCTGCCCTTC | CCCTGACATG | GGGCCACCAC | TAGCCTTTTA | TGGGCAGGCC | TGGCTGCTGG | 540 |
| TGGTTGGAAT | AACATCTGAC | TCCAGTGGGT | GTCTGTCACC | GTCTCCAGAC | AGGAGACAGA | 600 |
| GACAGAGGGT | CAAAGTTCAC | TATGGCTCTT | TGGGGCAATG | AAATGCTGTG | TTCTAGCCTC | 660 |
| TTGCCAGAAA | TCAGCCAAAG | TCAAGGAAAG | CCTGACTCCC | ACAGTTATCA | CAGAAAGAGC | 720 |
| ACCCACTTTC | CAGCCCAGAC | AGCTGCACCC | CAGCTGGGTC | CTGGCAGCCC | CAGCTTCAGC | 780 |
| CTGGGCGGTA | TGTTCCAGGC | CCCTCGATCA | TCTGACCCTA | ATATCACCCC | TTCACACCCC | 840 |
| CTCCACTTTC | TGCGGGAGCC | ACCCCGAACC | TTTGAATGGG | GGAGATCCTG | GAGGCTCTGC | 900 |
| AATTTTCAGT | GTAAACTGCC | TGGAGTTCCC | CACTTCACCC | TCATCTGGTT | CACCTGTGGA | 960 |
| CTCCCAACAG | AGCAGGCCCA | GGAAACGCGG | GGCCTCTGAG | GCCGG | | 1005 |

IDENTIFICATION OF DIFFERENTIALLY METHYLATED AND MUTATED NUCLEIC ACIDS

FIELD OF THE INVENTION

The present invention provides Methyl- (or Mutant-) Differential Display (MDD) methods and nucleic acid probes for detecting mutations and/or the methylation patterns of nucleic acids. Genes are frequently not methylated in the cells where they are expressed but are methylated in cell types where they are not expressed. Moreover, tumor cell DNA is frequently methylated to a different extent and in different regions than is the DNA of normal cells. The present invention is used for identifying which regions of the genome are methylated or mutated in different cell types, including cancerous cell types. The present invention also is used for identifying whether a tissue sample has a methylation or mutation pattern which is normal or like that of known cancer cells.

BACKGROUND OF THE INVENTION

DNA is often methylated in normal mammalian cells. For example, DNA is methylated to determine whether a given gene will be expressed and whether the maternal or the paternal allele of that gene will be expressed. See Melissa Little et al., *Methylation and p16: Suppressing the Suppressor*, 1 NATURE MEDICINE 633 (1995). While methylation is known to occur at CpG sequences, only recent studies indicate that CpNpG sequences may be methylated. Susan J. Clark et al., *CpNpGp Methylation in Mammalian Cells*, 10 NATURE GENETICS 20, 20 (1995). Methylation at CpG sites has been much more widely studied and is better understood.

Methylation occurs by enzymatic recognition of CpG and CpNpG sequences followed by placement of a methyl ($CH_3$) group on the fifth carbon atom of a cytosine base. The enzyme that mediates methylation of CpG dinucleotides, 5-cytosine methyltransferase, is essential for embryonic development—without it embryos die soon after gastrulation. It is not yet clear whether this enzyme methylates CpNpG sites. Peter W. Laird et al., *DNA Methylation and Cancer*, 3 HUMAN MOLECULAR GENETICS 1487, 1488 (1994).

When a gene has many methylated cytosines it is less likely to be expressed. K. Willson, 7 TRENDS GENET. 107–109 (1991). Hence, if a maternally-inherited gene is more highly methylated than the paternally-inherited gene, the paternally-inherited gene will give rise to more gene product. Similarly, when a gene is expressed in a tissue-specific manner, that gene will often be unmethylated in the tissues where it is active, but will be highly methylated in the tissues where it is inactive. Incorrect methylation is thought to be the cause of some diseases including Beckwith-Wiedemann syndrome and Prader-Willi syndrome. I. Henry et al., 351 NATURE 665, 667 (1991); R. D. Nicholls et al., 342 NATURE 281, 281–85 (1989).

The methylation patterns of DNA from tumor cells are generally different than those of normal cells. Laird et al., supra. Tumor cell DNA is generally undermethylated relative to normal cell DNA, but selected regions of the tumor cell genome may be more highly methylated than the same regions of a normal cell's genome. Hence, detection of altered methylation patterns in the DNA of a tissue sample is an indication that the tissue is cancerous. For example, the gene for Insulin-Like Growth Factor 2 (IGF2) is hypomethylated in a number of cancerous tissues, such as Wilm's Tumors, rhabdomyosarcoma, lung cancer and hepatoblastomas. Rainner et al. 362 NATURE 747–49 (1993); Ogawa, et al., 362 NATURE 749–51 (1993); S. Zhan et al., 94 J. CLIN. INVEST. 445–48 (1994); P. V. Pedone et al., 3 HUM. MOL. GENET. 1117–21 (1994); H. Suzuki et al., 7 NATURE GENET 432–38 (1994); S. Rainier et al., 55 CANCER RES. 1836–38 (1995).

The present invention is directed to a method of detecting differential methylation at CpNpG sequences by cutting test and control DNAs with a restriction enzyme that will not cut methylated DNA, and then detecting the difference in size of the resulting restriction fragments.

While methylation-sensitive restriction enzymes have been used for observing differential methylation in various cells, no commercial assays exist for use on human samples because differentially methylated sequences represent such a minute proportion of the human genome that they are not readily detected. The human genome is both highly complex, in that it contains a great diversity of DNA sequences, and highly repetitive, in that it contains a lot of DNA with very similar or identical sequences. The high complexity and repetitiveness of human DNA confounds efforts at detecting and isolating the minute amount of differentially methylated DNA which may be present in a test sample. The present invention remedies the detection problem by providing new procedures for screening a selected subset of the mammalian genome which is most likely to contain genetic functions.

The present invention provides techniques for detecting and isolating differentially methylated or mutated segments of DNA which may be present in a tissue sample in only minute amounts by using one or more rounds of DNA amplification coupled with subtractive hybridization to identify such segments of DNA. DNA amplification has been coupled with subtractive hybridization in the Representational Difference Analysis (RDA) procedures disclosed in U.S. Pat. No. 5,436,142 to Wigler et al. and Nikolai Lisitsyn et al., *Cloning the Differences Between Two Complex Genomes*, 259 SCIENCE 946 (1993). However, for the subtractive hybridization step of such RDA procedures to proceed in a reasonable time and with reasonable efficiency, only a subset of the genome can be examined. To accomplish this necessary reduction in the complexity of the sample DNA, Wigler et al. and Lisitsyn et al. disclose cutting DNA samples with restriction enzymes that cut infrequently and randomly. However, selection of enzymes which randomly cut the genome, means that the portion of the genome which is examined is not enriched for any particular population of DNA fragments. Thus, when RDA is used, only a random subset of the human genome, which includes repetitive elements, noncoding regions and other sequences which are generally not of interest, can be tested in a single experiment.

In contrast, the present invention is directed to methods which use enzymes that cut frequently and that specifically cut CG-rich regions of the genome. These enzymes are chosen because CG-rich regions of the genome are not evenly distributed in the genome—instead, CG-rich regions are frequently found near genes, and particularly near the promoter regions of genes. This means that the proportion of the genome that is examined by the present methods will be enriched for genetically-encoded sequences as well as regulatory sequences. Moreover, unlike the RDA method, the present methods selectively identify regions of the genome which are hypomethylated or hypermethylated by using enzymes which specifically cut non-methylated CG-rich sequences. The present invention therefore represents an improvement over RDA methods because of its ability to select DNA fragments which are likely to be near or to encode genetic functions.

SUMMARY OF THE INVENTION

The present invention provides probes and methods of detecting whether a CNGtriplet is hypomethylated or hypermethylated in a genomic DNA present in a test sample of cell.

The present invention provides a method of detecting whether a CNG triplet is hypomethylated or hypermethylated in a genomic DNA present in a test sample of cells which includes:
- a) isolating genomic DNA from a control sample of cells and a test sample of cells to generate a control-cell DNA and a test-cell DNA;
- b) cleaving the control-cell DNA and the test-cell DNA with a master restriction enzyme to generate cleaved control-cell DNA and cleaved test-cell DNA;
- c) preparing a probe from a DNA isolated by the present methods, for example, a DNA selected from the group consisting of SEQ ID NO:7–10;
- d) hybridizing the probe to the cleaved control-cell DNA and the cleaved test-cell DNA to form a control-hydridization complex and a test-hybridization complex; and
- e) observing whether the size of the control-hydridization complex is the same as the size of the test-hybridization complex;

wherein the master restriction enzyme cleaves a nonmethylated CNG DNA sequence but does not cleave a methylated CNG DNA sequence.

Similarly, the present invention provides a method of detecting whether a DNA site is mutated in a genomic DNA present in a test sample of cells which includes steps a) through e) above but where a detector restriction enzyme is used instead of the master restriction enzyme,
wherein the detector restriction enzyme does not cleave a mutated DNA site but does cleave a corresponding nonmutated DNA site.

The present invention also provides methods of isolating probes to detect hypomethylation or hypermethylation in a CNG triplet of DNA. In particular, the present invention provides a method of isolating a probe to detect hypomethylation in a CNG triplet of DNA which includes:
- a) cleaving a tester sample of genomic DNA with both a master restriction enzyme and a partner restriction enzyme to generate a cleaved tester sample;
- b) ligating a first set of adaptors onto master enzyme cut DNA ends of the cleaved tester sample to generate a first-tester amplification template;
- c) amplifying the first-tester amplification template to generate a first-tester amplicon by in vitro DNA amplification using primers that hybridize to the first set of adaptors;
- d) cleaving off the first adaptors from the first-tester amplicon and ligating a second set of adaptors onto DNA ends of the first-tester amplicon to generate a second-adaptor-tester which has second adaptor ends;
- e) melting and hybridizing the second-adaptor-tester with about a 10-fold to about a 10,000-fold molar excess of a driver DNA to generate a mixture of tester-tester product and tester-driver product;
- f) adding nucleotides onto DNA ends present in the mixture to make a blunt-ended tester-tester product and a blunt-ended tester-driver product;
- g) amplifying the blunt-ended tester-tester product and the blunt-ended tester-driver product by in vitro DNA amplification using primers that hybridize to second adaptor ends to generate a second-tester amplicon;
- f) isolating a discrete DNA fragment from the second tester amplicon as a probe to detect the hypomethylation or the hypermethylation in a CNG triplet of DNA;

wherein the master restriction enzyme cleaves a nonmethylated CNG DNA sequence but does not cleave a methylated CNG DNA sequence;

wherein the partner restriction enzyme cleaves DNA to produce DNA fragments with a complexity of about 5% to about 25% of the genomic DNA in a size range which can be amplified by a DNA amplification enzyme; and wherein the driver DNA is cut with both the master restriction enzyme and the partner restriction enzyme and amplified using primers that recognize DNA ends cut by the master restriction enzyme.

Similarly, when the present invention provides a method of isolating a probe to detect hypermethylation in a CNG triplet of DNA, normal DNA is used instead of the tester DNA and the normal amplicon is annealed and hybridized with a molar excess of tester driver DNA.

Moreover the present methods are used to isolate probes to detect a mutation in a test sample of genomic DNA by using a detector enzyme instead of a partner restriction enzyme, wherein the detector restriction enzyme cleaves a normal DNA site but not a mutant DNA site.

The present invention further provides a kit for detecting hypomethylation in a CNGtriplet of DNA which is present in a test tissue sample which includes a DNA or a probe isolated by the methods of the present invention, for example, a DNA having SEQ ID NO:7–10.

BRIEF DESCRIPTIONS OF THE DRAWINGS

FIG. 1 provides a schematic diagram of how the MDD technique generally selects for DNA fragments which have non-methylated CG-rich ends. Driver DNA is isolated from a normal cell or tissue sample of the same tissue-type as the tester cell DNA. Tester DNA is isolated from a cell or tissue sample which likely has a mutation or a difference in the extent to which its DNA is methylated. Tester and driver DNAs are cleaved by the master (M) and partner (P) restriction enzymes. The master enzyme will not cleave DNA at sites that have a methyl group (superscript "m") but will cleave at sites which are nonmethylated (superscript m having a line drawn through it). The partner enzyme cleaves the DNA into a size and a complexity appropriate for DNA amplification and subtractive hybridization. After cleavage, a small target fragment is completely excised from the tester DNA but not from the driver DNA. Adaptors (m-linkers) which hybridize only to master-enzyme-cut DNA ends are ligated onto the tester and driver DNA fragments. Unique target DNAs from the tester sample will have adaptors on both ends. Upon DNA amplification using a primer that recognizes only the adaptor sequences, only DNA fragments with adaptors on both ends will be efficiently amplified.

FIG. 2 depicts an agarose gel containing electrophoretically separated DNA fragments isolated by MDD from malignant B-cells derived from Chronic Lymphocytic Leukemia (CLL) patients. Lane A contains the different products isolated from CLL patient #111. Lane M contains Hae III 0174 DNA size markers. As illustrated, the present MDD methods give rise to discrete fragments of DNA which can readily be isolated and subcloned or used as probes for identifying the methylation patterns of genomic DNA samples from different cell types.

FIG. 3 depicts a Southern Blot of MspI-digested tester (T) and driver (D) DNA hybridized with the CLL58 probe. The lane labeled "probe #58" contains a clone of the CLL58 probe. The lane labeled "T" contains amplified 2 μg CD5+ B-cell DNA, whereas the lane "D" contains 2 μg amplified neutrophil DNA. Both T and D DNA samples were isolated from the CLL patient #111 and amplified by the MDD method. As a positive control, probe CLL58 hybridizes strongly to itself Probe CLL58 also hybridizes strongly with the tester DNA but only weakly with the driver amplicon DNA—this is due to DNA hypomethylation in the tester DNA.

FIG. 4 depicts a Southern Blot of MspI-digested DNA hybridized with the CLL58 probe. The lane labeled "probe #58" contains a clone of the CLL58 probe. The lane labeled "T" contains 6 μg of CD5+ B-cell DNA, whereas lane "N" contains 6 μg of neutrophil DNA, each isolated from the CLL patient #111. As a positive control, probe CLL58 hybridizes strongly to itself. Probe CLL58 hybridizes with a lower band and several upper bands in B-cell DNA (lane T), while comparatively hybridizing much less with the lower band in neutrophil cell DNA (lane N). The lesser hybridization to the lower band in neutrophil DNA is due to DNA methylation which prevents complete excision of that fragment. Hence, the CLL58 probe provides a comparative methyl-differential display in B-cells and neutrophil cells.

FIG. 5 depicts an agarose gel after electrophoresis of the different final products isolated from breast patient #13 (lane A), patient #14 (lane B) and breast patient #4 (lane C) using the MDD technique. Lane MW contains Hae III 0174 DNA size markers.

FIG. 6a depicts a Southern Blot of MspI-digested tester (T) and driver (D) DNA hybridized with the BR50 probe. The lane labeled "probe #50" contains a clone of the BR50 probe. The lane labeled "T" contains amplified breast tumor cell DNA, whereas the lane "D" contains amplified normal breast cell DNA. Both T and D DNA samples were isolated from the breast patient #14 and amplified by the MDD method. As a positive control, probe BR50 hybridizes strongly to itself. Probe BR50 also hybridizes strongly with the tester DNA but only weakly with the driver amplicon DNA—this is due to DNA hypomethylation in the tester DNA.

FIG. 6b depicts a Southern Blot of MspI-digested tester (T) and driver (D) DNA hybridized with the BR104 probe. The lane labeled "probe #104" contains a clone of the BR104 probe. The lane labeled "T" contains amplified breast tumor cell DNA, whereas the lane "D" contains amplified normal breast cell DNA. Both T and D DNA samples were isolated from the breast patient #13 and amplified by the MDD method. As a positive control, probe BR104 hybridizes strongly to itself Probe BR104 also hybridizes strongly with the tester DNA but only weakly with the driver amplicon DNA—this is due to DNA hypomethylation in the tester DNA.

FIG. 6c depicts a Southern Blot of MspI-digested tester (T) and driver (D) DNA hybridized with the BR254 probe. The lane labeled "probe #254" contains a clone of the BR254 probe. The lane labeled "T" contains amplified breast tumor cell DNA, whereas the lane "D" contains amplified normal breast cell DNA. Both T and D DNA samples were isolated from the breast patient #4 and amplified by the MDD method. As a positive control, probe BR254 hybridizes strongly to itself Probe BR254 also hybridizes strongly with the tester DNA but only weakly with the driver amplicon DNA—this is due to DNA hypomethylation in the tester DNA.

FIG. 7a depicts a genomic Southern Blot of MspI-digested DNA hybridized with a probe BR50 isolated from a breast cancer patient. The lane labeled "probe #50" contains a clone of the isolated BR50 probe. The lane labeled "T" contains 6 μg of B-cell DNA, whereas lane "N" contains 6 μg of normal breast DNA, each isolated from the breast cancer patient #14. As a positive control, probe BR50 hybridizes strongly to itself Probe BR50 hybridizes strongly with a lower band and weakly with a medium band in breast tumor DNA (lane T). However, in normal breast cell DNA (lane N), probe BR50 hybridizes much less with the lower band and only weakly to an upper band. The lesser hybridization to the lower band in normal breast DNA is due to DNA methylation which prevents complete excision of that fragment. Hence, the BR50 probe provides a comparative methyl-differential display in tumor and normal breast cells.

FIG. 7b depicts a genomic Southern Blot of MspI-digested DNA hybridized with a probe BR104 isolated from a breast cancer patient. The lane labeled "probe #104" contains a clone of the isolated BR104 probe. The lane labeled "T" contains 6 μg of tumor DNA, whereas lane "N" contains 6 μg of normal breast cell DNA, each isolated from the breast cancer patient #13. As a positive control, probe BR104 hybridizes strongly to itself Probe BR104 hybridizes strongly with a lower band and weakly with a medium band in tumor DNA (lane T). However, in normal breast cell DNA (lane N), probe BR104 hybridizes lightly with the lower band and moderately with middle and upper bands. The lesser hybridization to the lower band in normal breast DNA is due to DNA methylation which prevents complete excision of that fragment. Hence, the BR104 probe provides a comparative methyl-differential display in tumorous and normal breast cells.

FIG. 7c depicts a genomic Southern Blot of MspI-digested DNA hybridized with a probe BR254 isolated from a breast cancer patient. The lane labeled "probe #254" contains a clone of the isolated BR254 probe. The lane labeled "T" contains 6 μg of B-cell DNA, whereas lane "N" contains 6 μg of normal breast cell DNA, each isolated from the breast cancer patient #4. As a positive control, probe BR254 hybridizes strongly to itself. Probe BR254 hybridizes strongly with a lower band and with an upper band in tumor DNA (lane T). However, in normal breast cell DNA (lane N), probe BR254 hybridizes only with the upper band. The lack of hybridization to the lower band in normal breast DNA is due to DNA methylation which prevents excision of that fragment. Hence, the BR254 probe provides a comparative methyl-differential display in tumorous and normal breast cells.

FIG. 8 depicts a Southern blot of MspI-digested genomic DNA from five different breast cancer patients which was hybridized with the BR50 probe. The number for each patient is listed above the bracket. The hybridization patterns of tumor (T) and matched normal (N) DNAs from each patient are provided for comparison. The lane labeled "probe #50" contains a clone of the isolated BR50 probe. The lane labeled "T" contains 6 μg of DNA isolated from a tumor, whereas lane "N" contains 6 μg of DNA from normal breast tissue. As a positive control, probe BR50 hybridizes strongly to itself For each of the five patients, probe BR50 hybridizes strongly with a lower band and less strongly with an upper band in the tumor DNA samples (T). However, probe BR50 hybridizes much less with the lower band in the normal DNA samples (N). The lesser hybridization to the lower band in normal DNA is due to DNA methylation which prevents complete excision of that fragment. Hence, the BR50 probe provides a comparative methyl-differential display in breast tumor and normal DNA samples.

FIG. 9 depicts a Southern blot of MspI-digested genomic DNA from four different breast cancer patients which was hybridized with the BR104 probe. The number for each patient is listed above the bracket. The hybridization patterns of tumor (T) and matched normal (N) DNAs from each patient are provided for comparison. The lane labeled "probe #104" contains a clone of the isolated BR104 probe. As a positive control, probe BR104 hybridizes strongly to itself The lanes labeled "T" contain 6 $\mu$g of DNA isolated from a breast tumor, whereas the lanes labeled "N" contain 6 $\mu$g of DNA from normal breast tissue. For tumor DNA from each of the four patients, probe BR104 hybridizes with a lower band and a middle band. In the normal DNA, the probe hybridizes mainly with the middle band and an upper band. The lesser hybridization to the lower band in normal DNA is due to DNA methylation which prevents complete excision of that fragment. Hence, the BR104 probe provides a comparative methyl-differential display in breast tumor and normal breast DNA samples.

FIG. 10 depicts a Southern blot of MspI-digested genomic DNA from four different breast cancer patients which was hybridized with the BR254 probe. The number for each patient is listed above the bracket. The hybridization patterns of tumor (T) and matched normal (N) DNAs from each patient are provided for comparison. The lane labeled "probe #254" contains a clone of the isolated BR254 probe. The lane labeled "T" contains 6 $\mu$g of DNA isolated from a breast tumor, whereas lane "N" contains 6 $\mu$g of DNA from normal breast tissue. As a positive control, probe BR254 hybridizes strongly to itself For each of the four patients, probe BR254 hybridizes strongly with a lower band and less strongly with an upper band in the tumor DNA samples (T). However, probe BR254 hybridizes much less with the lower band in the normal DNA samples (N). The lesser hybridization to the lower band in normal DNA is due to DNA methylation which prevents complete excision of that fragment. Hence, the BR254 probe provides a comparative methyl-differential display in breast tumor and normal DNA samples.

FIG. 11 depicts an amplification pattern detected by probe BR254 in DNA isolated from a breast tumor biopsy. FIG. 12 provides a Southern blot of normal (N) and tumor (T) DNA from breast cancer patient #23 which was digested with MspI and hybridized with the BR254 probe. Both the N and T lanes contain 6 $\mu$of DNA. The lane labeled "probe #254" contains a clone of the isolated BR254 probe, which hybridizes to itself In the tumor DNA, the BR254 probe hybridizes very, very strongly to a DNA fragment to which it hybridizes only moderately in normal DNA. This indicates that the breast tumor DNA of patient #23 has a highly amplified region of genomic DNA which is not present in her normal DNA.

FIG. 12 depicts a Southern blot of MspI-digested genomic DNA from five different ovarian cancer patients which was hybridized with the BR50 probe. The number for each patient is listed above the bracket. The hybridization patterns of 6 $\mu$g primary tumor DNA (T or Tl), 6 $\mu$metastatic tumor DNA (Tm) and 6 $\mu$g normal ovarian DNA (N) from these patients are provided for comparison. The lane labeled "probe #50" contains a clone of the isolated BR50 probe. The lane labeled "T" contains 6 $\mu$g of DNA isolated from a ovarian tumor, whereas lane "N" contains 6 $\mu$g of DNA from normal ovarian tissue. As a positive control, probe BR50 hybridizes strongly to itself. In primary tumor DNAs, the probe predominantly hybridizes with the lower bands, and slightly hybridizes with the upper bands. In metastatic tumor DNAs, the probe only hybridizes with the lower bands. In normal DNAS, the probe hybridized with the lower bands and the upper bands. The lesser hybridization to the lower band in normal DNA is due to DNA methylation which prevents complete excision of that fragment. Hence, the BR50 probe provides a comparative methyl-differential display in ovarian tumor and normal DNA samples. The degree of DNA hypomethylation may be related to the progress of the disease.

FIG. 13 depicts a Southern blot of MspI-digested genomic DNA from four different ovarian cancer patients which was hybridized with the BR254 probe. The number for each patient is listed above the bracket. The hybridization patterns of tumor (T) and matched normal (N) DNAs from each patient are provided for comparison. The lane labeled "probe #254" contains a clone of the isolated BR254 probe. The lane labeled "T" contains 6 $\mu$g of DNA isolated from a ovarian tumor, whereas lane "N" contains 6 $\mu$g of DNA from normal ovarian tissue. As a positive control, probe BR254 hybridizes strongly to itself. For each of the four patients, probe BR254 hybridizes with a lower band and with an upper band in the tumor DNA samples (T). However, probe BR254 hybridizes only with the upper band in the normal DNA samples (N). The lack of hybridization to the lower band in normal DNA is due to DNA methylation which prevents excision of that fragment. Hence, the BR254 probe provides a comparative methyl-differential display in ovarian tumor and normal DNA samples.

FIG. 14 depicts a Southern blot of MspI-digested genomic DNA from six different colon cancer patients which was hybridized with the BR254 probe. The number for each patient is listed above the bracket. The hybridization patterns of 6 $\mu$g tumor (T) and 6 $\mu$g matched normal (N) DNAs from each patient are provided for comparison. The lane labeled "probe #254" contains a clone of the isolated BR254 probe as a positive control to show that probe BR254 hybridizes strongly to itself In the tumor DNA, the probe hybridizes with lower and upper bands with equal intensity. In the normal DNA, the probe hybridizes mainly with the lower band. Hence, the BR254 probe detects alteration of DNA methylation in colon cancer DNA.

DETAILED DESCRIPTION OF THE INVENTION

Figure 1A:
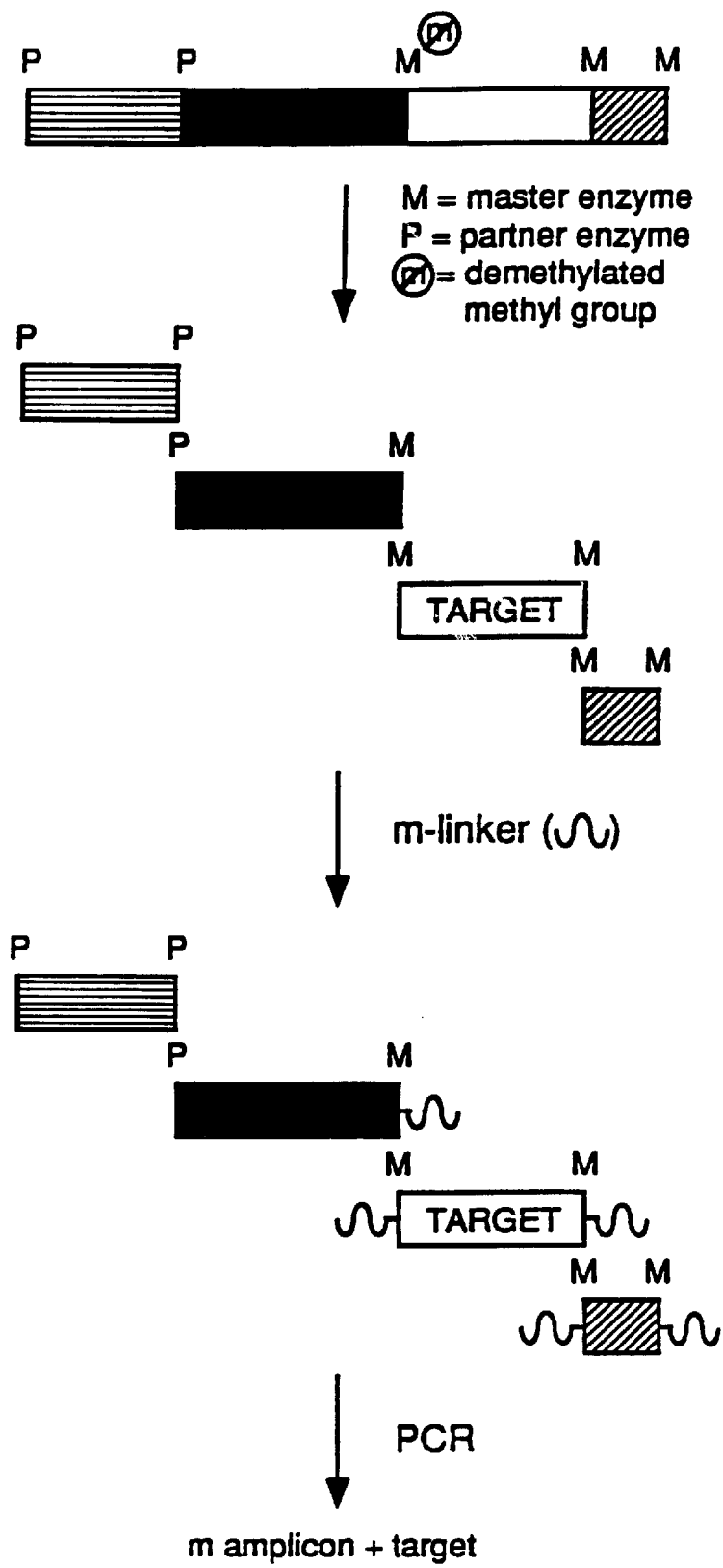

The present invention provides methods and probes for detecting and isolating DNA sequences which are mutated or methylated in one tissue type but not in another. These methods are herein named Methyl- (or Mutant-) Differential Display ("MDD") methods. These MDD methods, and probes that are isolated by MDD, are useful inter alia for identifying genes that are expressed in a tissue-specific manner. Moreover, the present MDD methods and probes are useful for detecting cancerous cells, viruses, bacteria, point mutations, amplificiatioms, deletions and genomic rearrangements.

To detect whether a DNA sequence is differentially methylated, the present invention uses methylation-sensitive restriction enzymes to cleave tester and control DNA's. These methylation-sensitive restriction enzymes will cut their DNA recognition sites when those sites are not methylated but do not cut the DNA site if it is methylated. Hence, a non-methylated tester DNA will be cut into smaller sizes than a methylated control DNA. Similarly, a hypermethylated tester DNA will not be cleaved and will give rise to larger fragments than a normally non-methylated control DNA.

The present invention is particularly useful for detecting and isolating DNA fragments that are normally methylated but which, for some reason, are non-methylated in a small proportion of cells. Such DNA fragments may normally be methylated for a number of reasons. For example, such DNA fragments may be normally methylated because they contain, or are associated with, genes that are rarely expressed, genes that are expressed only during early development, genes that are expressed in only certain cell-types, and the like.

While highly expressed genes are frequently unmethylated, those highly expressed genes are often not very interesting because they are "housekeeping genes" which contribute to generalized cellular functions and cellular survival, rather than to the determination of what makes one cell-type different from another. Moreover, highly expressed genes have generally already been isolated and characterized.

Unlike the housekeeping genes, non-methylated but normally-methylated, DNA fragments are present in just a small proportion of cells. Therefore, it is very difficult to detect or isolate those fragments and to distinguish them from non-methylated housekeeping genes. The present invention solves this problem by using a combination of DNA amplification and hybridization/subtraction techniques. The amplication steps enrich the genomic DNA sample with small DNA fragments that have both 5' and 3' ends cut by the methylation-sensitive enzyme. The hybridization/subtraction steps eliminate fragments encoding non-methylated housekeeping genes and fragments which are cut on only one end by the methylation-sensitive enzyme. Several rounds of amplification and hybridization/subtraction can be used if a discrete number of fragments are not isolated with the first round.

The fragments isolated by MDD are cut on both ends by the methylation-sensitive master enzyme because only fragments cut on both ends with the master enzyme are efficiently amplified. This is accomplished by using primers during DNA amplification that recognize only the master-enzyme-cut DNA ends. Such primer specificity is created by adding adaptors to the DNA ends of a sample cut with both the master enzyme and a partner restriction enzyme. The adaptors have unique sequences which hybridize with the DNA amplification primers. The partner enzyme is used to generate a mixture of DNA fragments of an appropriate size and complexity for DNA amplification but also creates a population of DNA molecules which will not accept the adaptors because they have partner-enzyme-cut ends.

Similarly, for detecting and isolating fragments which contain a mutation, DNA fragments are cut with a master enzyme and a partner (detector) enzyme, where the partner (detector) enzyme may cut normal DNA but which will not cut mutated DNA. The master enzyme normally used for MDD is a methylation-sensitive enzyme which recognizes and cuts CG-rich sites in genomic DNA. However, for detecting and isolating fragments that contain a mutation, nonmethylation sensitive master enzymes can also be used. Any restriction enzyme can be used as a master restriction enzyme for detecting and isolating mutations so long as it cuts at a different sequence than the detector enzyme. However, a master enzyme which cuts in CG-rich regions is preferred because it selects for regions associated with genes while the detector enzyme identifies and permits isolation of the mutation by cutting only the nonmutant DNA fragments.

To confirm whether fragments isolated by the present MDD methods can detect differentially methylated or mutated DNA sites, they are tested as probes on genomic DNAs which are cut with methylation-sensitive or mutant-detector enzymes, respectively. If the probe detects a different size fragment in DNA which is known, or suspected to be, hypomethylated, hypermethylated or mutated than in normal DNA, then the probe can detect differentially methylated or mutated DNA sites.

DNA fragments isolated by the present methods can therefore constitute probes, for example, for detecting hypomethylation, hypermethylation or mutation in DNA fragments which are normally methylated.

In particular, the present invention provides a method of isolating probes to detect hypomethylation in a CNG triplet of DNA which includes:

a) cleaving a tester sample of genomic DNA with a master restriction enzyme and a partner restriction enzyme to generate a cleaved tester sample;

b) amplifying the cleaved tester sample using primers that recognize DNA ends cut by the master restriction enzyme, to generate a first tester amplicon;

c) melting and hybridizing the first test amplicon with a driver DNA to generate a tester-tester product and a tester-driver product;

d) adding nucleotides to the ends of the tester-tester product and the tester-driver product to make a blunt-ended tester-tester product and a blunt-ended tester-driver product;

e) amplifying the blunt-ended tester-tester product and the blunt-ended tester-driver product by using primers which recognize only master-enzyme-cut DNA ends, to produce a second tester amplicon;

f) isolating a discrete DNA fragment from the second tester amplicon as a probe to detect hypomethylation a CNG triplet of DNA;

wherein the master restriction enzyme cleaves a nonmethylated CNG DNA sequence but does not cleave a methylated CNG DNA sequence;

wherein the partner restriction enzyme cleaves DNA to produce DNA fragments with a complexity of about 5% to about 25% of the genomic DNA in a size range which can be amplified by a DNA amplification enzyme; and wherein the driver DNA is cut with both the master restriction enzyme and the partner restriction enzyme, and then amplified by using primers that recognize DNA ends cut by the master restriction enzyme.

In another embodiment, the master-enzyme-cut DNA ends are distinguished from the partner-enzyme-cut DNA ends by ligating a first set of adaptors onto master-enzyme-cut DNA ends of the cleaved tester sample to generate a first-tester amplification template. This first-tester amplification template is then amplified to generate a first-tester amplicon by in vitro DNA amplification using primers that hybridize to the first set of adaptors. Hence, only DNA fragments which were cut by the master restriction enzyme will be amplified. The first adaptors are then cleaved off the first-tester amplicon and a second set of adaptors is ligated onto master-enzyme-cut DNA ends of the first-tester amplicon to generate a second-adaptor-tester which has second adaptor ends. As before, this tester DNA is melted and hybridized with a large molar excess of a driver DNA to generate a mixture of tester-tester product and tester-driver product. The DNA ends of these products are made blunt by adding nucleotides and the blunt-ended tester-driver product is amplified the blunt-ended tester-tester product and the blunt-ended tester-driver product by in vitro DNA amplification using primers that hybridize to second adaptor ends. This generates a second-tester amplicon from which a discrete DNA fragments can be isolated as probes to detect the hypomethylation in a CNG triplet of DNA.

As used herein, hypomethylation means that at least one cytosine in a CG or CNG di- or tri-nucleotide site in genomic DNA of a given cell-type does not contain $CH_3$ at the fifth position of the cytosine base. Cell types which may have hypomethylated CGs or CCGs include any cell type which may be expressing a non-housekeeping function. This includes both normal cells that express tissue-specific or cell-type specific genetic functions, as well as tumorous, cancerous, and similar cell types. Cancerous cell types and conditions which can be analyazed, diagnosed or used to obtaining probes by the present methods include Wilm's cancer, breast cancer, ovarian cancer, colon cancer, kidney cell cancer, liver cell cancer, lung cancer, leukemia, rhabdomyosarcoma, sarcoma, and hepatoblastoma.

Genomic DNA samples can be obtained from any mammalian body fluid, secretion, cell-type, or tissue, as well as any cultured cell or tissue.

The present MDD technique involves preparation of a driver DNA and a tester DNA. A driver DNA is genomic DNA from a "normal" cell type. A tester DNA is genomic DNA from a "test" cell type which may have mutated DNA sites, hypermethylated DNA sites or non-methylated DNA sites in place of the normal DNA at that site. Such normal cell types are cells of the same tissue-type as the "test" cell type, but which are normally methylated and are not mutated. Test cell tyes include cells that express tissue or cell-specific functions, cancer cells, tumor cells and the like. For example, if breast cancer cells are selected as the test cell type, the normal cell type would be breast cells that are not diseased or cancerous. Preferably, test and normal cell types are isolated from the same person.

After isolation, the tester DNA and the driver DNA are separately cut with both the master and partner restriction enzymes. As provided by the present invention, the master restriction enzyme cleaves a CNG DNA sequence. The master restriction enzyme produces sticky ends, rather than blunt ends, when it cuts. In general, the master enzyme used in the present methods cleaves only non-methylated CNG DNA sequences and does not cleave methylated CNG DNA sequences. However, for selected applications a nonmethylation sensitive master enzyme can be used, for example, for detecting and isolating mutations. For detecting and isolating hypomethylated DNA sites, a methylation-sensitive master enzyme should be used, for example, the MspI restriction enzyme which recognizes and cleaves DNA at nonmethylated CCGG but will not cleave the CCGG sequence when the outer cytosine is methylated. Master restriction enzymes contemplated by the present invention include MspI, BsiSI, Hin2I and the like. In a preferred embodiment, MspI is used as the master restriction enzyme for detecting and isolating a DNA fragment containing a hypomethylated site.

According to the present invention, a partner restriction enzyme cleaves DNA to produce DNA fragments with a complexity of about 5% to about 25% of the genomic DNA in a size range which can be amplified by a DNA amplification enzyme. As used herein, the complexity of mixture of DNA fragments is the number of different DNA fragments within a selected size range. When mammalian DNA is used, the present methods can effectively screen a DNA sample containing about 1% to about 25% of the mammalian genome. In a preferred embodiment, a DNA sample has about 5% to about 15% of the total DNA sequences in the mammalian genome. In an especially preferred embodiment, the DNA sample has about 10% of the total DNA sequences in the mammalian genome.

According to the present invention, the size range of DNA fragments in a sample of genomic DNA is that size range which can be amplified by in vitro DNA amplification. When polymerase chain reaction ("PCR") is used, that size range is about 2000 base pairs (bp) to about 75 bp. Preferably the selected size range is about 1500 bp to about 100 bp. More preferably the selected size is about 1000 bp to about 150 bp.

As used herein, the preferred size is generated by the action of both the master and partner restriction enzymes. Hence, if the partner restriction enzyme generates a population of genomic DNA fragments which are about 1000 bp or smaller, but, in combination with the master restriction enzyme a population of fragments which are less than 50 bp is generated, a different set of partner and master enzymes is preferably used.

Also according to the present invention, the partner restriction enzyme cleaves DNA to produce ends that are neither homologous nor complementary to a sticky end produced by the master restriction enzyme.

Any convenient restriction enzyme is used as a partner restriction enzyme to identify CNG sited that are hypomethylated, so long as the appropriate complexity and size of DNA fragments are generated. For convenience, a partner restriction enzyme that operates under the same conditions as the master restriction enzyme may be used. For example, MseI is a good partner restriction enzyme which can be used under the same conditions as the preferred MspI master restriction enzyme. When the preferred MspI master restriction enzyme is used, the partner restriction enzyme preferably recognizes and cuts a 4-nucleotide sequence. Moreover, in a preferred embodiment, the partner restriction enzyme cuts an AT-rich site or generates a blunt end to avoid any ligation of adaptors, which are designed to attach to master enzyme cut ends, onto the ends generated by the partner enzyme. Preferred partner restriction enzymes include MseI, Sau3A, RsaI, TspEI, MaeI, NiaIII, DpnI and the like.

Cleavage methods and procedures for selecting restriction enzymes for cutting DNA at specific sites are known to the skilled artisan. For example, many suppliers of restriction enzymes provide information on conditions and types of DNA sequences cut by specific restriction enzymes, including New England BioLabs, Pro-Mega Biochems, Boehringer-Mannheim and the like. Sambrook et al. provide a general description of methods for using restriction enzymes and other enzymes. See Sambrook et al., 1989 *Molecular Cloning: A Laboratory Manual*, Vols. 1–3 (Cold Spring Harbor Press, Cold Spring Harbor, N.Y.).

After cleaving the DNA with the master and partner restriction enzymes, a set of adaptors is hybridized and ligated onto the sticky DNA ends produced by the master restriction enzyme. The adapters are selected so that they will ligate to the CG-rich ends of the DNA cut by the master restriction enzyme but not to the ends of the fragments that were cut with the partner restriction enzyme. Because the only the DNA ends of fragments in the tester and driver genomic DNA samples will be single-stranded, adaptors need not be longer than about 12 nucleotides to specifically recognize and hybridize to the master enzyme-cut ends. However, the adaptors are chosen not only to ligate to DNA ends cut by the master restriction enzyme, but also to be a good size and DNA sequence to act as recognition sites for primers used during DNA amplification. Adaptors are chosen so that, when the mixture of master and partner enzyme cut DNA fragments is amplified using primers that hybridize to those adaptors, only those fragments that have the adaptor and thus were cut with the master restriction enzyme will be amplified. Hence, after hybridization and ligation the adaptor ends should have a unique sequence and be of sufficient length to be a unique recognition site for primers selected for in vitro DNA amplification.

Preferred sets of adaptors of the present invention include those of SEQ ID NO:1–6. As used herein:

the MSA24 adaptor has SEQ ID NO:1—
CTCGTCGTCAGGTCAGTGCTTCAC the MSA12 adaptor has SEQ ID NO:2—
CGGTGAAGCACT the MSB24 adaptor has SEQ ID NO:3—
TAGAGCCACGTAGCTGCTGTAGTC the MSB12 adaptor has SEQ ID NO:4—
CGGACTACAGCA the MSC24 adaptor has SEQ ID NO:5—
ACCGTGGACTGGATAGGTTCAGAC and the MSC12 adaptor has SEQ ID NO:6—
CGGTCTGAACCT.

In one embodiment, the SEQ ID NOS:1 and 2 (MSA24 and MSA12) adaptors are single-stranded and are used as the first set of adaptors. These single-stranded adaptors are annealed and hybridized onto DNA ends cut with the master restriction enzyme and then ligated to those DNA ends by incubation with ligase. Both the tester and driver DNAs receive the first set of adaptors. Thus, the master-cut ends of both the tester and driver DNAs will have adaptors while DNA ends cut with the partner enzyme, from either the tester or driver, will have no such adaptors.

The two samples are then separately amplified by known DNA amplification procedures using primers that hybridize to the adaptors. For example, when the SEQ ID NO:1 and 2 adaptors are used, an oligonucleotide having SEQ ID NO:1 can be used as a primer for DNA amplication of only the master enzyme cut DNA fragments. This generates a tester amplicon and a driver amplicon. In both the tester and driver amplicons, only fragments which are cut with the master restriction enzyme will be amplified.

DNA amplification procedures for use in the present MDD methods include any in vitro amplification procedure which provides sequence-specific synthesis of a nucleic acid fragment relative to the complex bulk of nucleic acid present in a sample. The specificity of the process is determined by enzymatic recognition of a specific sequence or by the oligonucleotide primers which are capable of hybridizing only with selected adaptors that are added onto the ends of master restriction cut DNA fragments.

In vitro DNA amplification techniques are known in the art. A review of such techniques can be found in Kwoh et al., 8 *Am. Biotechnol. Lab.* 14 (1990). In vitro nucleic acid amplification techniques include polymerase chain reaction (PCR), transcription-based amplification system (TAS), self-sustained sequence replication system (3SR), ligation amplification reaction (LAR), ligase-based amplification system (LAS), Qβ RNA replication system and run-off transcription.

PCR is a preferred method for DNA amplification. PCR synthesis of DNA fragments occurs by repeated cycles of heat denaturation of DNA fragments, primer annealing onto the adaptor ends of the master-cut DNA fragment, and primer extension. These cycles can be performed manually or, preferably, automatically. Thermal cyclers such as the Perkin-Elmer Cetus cycler are specifically designed for automating the PCR process, and are preferred. The number of cycles per round of synthesis can be varied from 2 to more than 50, and is readily determined by considering the source and amount of the nucleic acid template, the desired yield and the procedure for detection of the synthesized DNA fragment.

PCR techniques and many variations of PCR are known. Basic PCR techniques are described by Saiki et al. (1988 *Science* 239:487–491) and by U.S. Pat. Nos. 4,683,195, 4,683,202 and 4,800,159, which are incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95° C.) and incubation at a temperature permitting primer: adaptor hybridization and copying of the master-cut DNA fragment by the amplification enzyme. Heat stable amplification enzymes like the pwo, *Thermus aquaticus* or *Thermococcus litoralis* DNA polymerases are commercially available which eliminate the need to add enzyme after each denaturation cycle. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include pwo, *Escherichia coli* DNA polymerase I, Klenow fragment of *E. coli* DNA polymerase I, T4 DNA polymerase, T7 DNA polymerase, *Thermus aquaticus* (Taq) DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase. Preferred amplification enzymes are the pwo and Taq polymerases. The pwo enzyme is especially preferred because of its fidelity in replicating DNA.

The length of the primers for use in MDD depends on several factors including the nucleotide sequence and the temperature at which these nucleic acids are hybridized or used during in vitro nucleic acid amplification. The considerations necessary to determine a preferred length for an oligonucleotide primer are well known to the skilled artisan. For example, as is known to the skilled artisan, the length of a short nucleic acid or oligonucleotide can relate to its hybridization specificity or selectivity. Because the tester and driver samples contain a complex mixtures of nucleic acids, primers which are shorter than about 12 nucleotides may hybridize to more than one site in the test genomic DNA, and accordingly would not have sufficient hybridization selectivity for amplifying only the master-cut fragments. However, a 12- to 15-nucleotide sequence is generally represented only once in a mammalian genome (Sambrook et al. 1989 *Molecular Cloning: A Laboratory Manual*, Vol. 2, Cold Spring Harbor Press, Cold Spring Harbor, N.Y.; pp. 11.7–11.8). Accordingly, to eliminate amplification of fragments which do not have adaptors, primers are chosen which are generally at least about 14 nucleotides long.

Preferably, the present primers are at least 16 nucleotides in length. More preferred primers are at least 17 nucleotides in length (Sambrook et al., pp. 11.7–11.8).

After amplification, the first set of adaptors are removed from the ends of the tester and driver amplicons by cleavage with the master restriction enzyme. Cleavage with the master restriction enzyme preserves the original ends of the fragments and removes all DNA which was not present in the tester DNA as originally isolated.

A second set of adaptors are ligated to the tester amplicon, but not to the driver amplicon. This generates a second-adaptor-tester sample. The second set of adaptors is selected so that they do not have the same sequence as the first set of adaptors and so that they hybridize, and hence ligate, only to DNA ends cut by the master restriction enzyme. The second set of adaptors should also form a good recognition site for primers which are used during DNA amplification.

During DNA amplification, non-methylated DNA fragments which are normally present in all cell types, and which may not be of interest, will also be amplified because they will have adaptors on their ends. At least one round of subtraction/hybridization followed by DNA amplification is used by the present MDD methods to remove these nonmethylated DNA fragments which likely encode "housekeeping" functions.

In general, the present MDD techniques remove "housekeeping" sequences by hybridizing the amplified tester DNA with a large molar excess of amplified driver DNA and amplifying only the tester-tester hybrids which have perfectly hybridized ends because those perfectly hybridized ends are the only sites recognized by the primers used for DNA amplification.

In particular, the amplified tester DNA (called the first test amplicon or the second-adaptor-tester) is mixed with a large molar excess of amplified driver DNA. The mixture is denatured, then renatured. As used herein, a large molar excess of driver to tester DNA is about a 10-fold to about a 10,000-fold molar excess of driver DNA to tester DNA. In a preferred embodiment the tester DNA is melted and hybridized with about a 10-fold to about a 1000-fold molar excess of a driver DNA. In a more preferred embodiment, the tester DNA is melted and hybridized with about a 100-fold molar excess of a driver DNA. Stringent hybridization conditions are preferably used during renaturation to maximize the formation of fragments with few mismatches.

The skilled artisan can vary the hybridization conditions used during MDD to achieve optimal hybridization of unique tester DNA fragments to their tester homologue. Conditions for achieving optimal hybridization are known to the skilled artisan and generally include temperature and salt concentrations permitting selective hybridization between two highly homologous DNA fragments, e.g. stringent hybridization conditions. Stringent conditions permit little or no detectable hybridization between mismatched driver or tester fragments, that is between fragments that have dissimilar sequences, particularly at the ends. Hybridization techniques are described, for example, in Sambrook et al., 1989 *Molecular Cloning: A Laboratory Manual*, Vols. 1–3 (Cold Spring Harbor Press, Cold Spring Harbor, N.Y.).

The ends of the renatured fragments are then filled in using a DNA polymerase, e.g. Taq or pwo polymerase. Such a "filling in" reaction makes the DNA fragments blunt-ended but does not eliminate any internally mismatched or unhybridized regions. To eliminate such mismatched hybrids, the renatured fragments may be treated with a nuclease that will remove single-stranded regions and mismatched nucleotides in the renatured fragments. For example, S1 nuclease, mung bean nuclease and the like can be used to eliminate mismatched hybrids. The nuclease will also cleave off mismatched nucleotides at the ends of either the tester or the driver fragment. Hence, mismatched hybrids will have ends that do not contain second adaptor ends. Only the single-stranded tester fragments with second adaptor ends that faithfully hybridize to an exact tester homologue will end up with a second adaptor end.

The subtraction/hybridization mixture is then amplified by in vitro DNA amplification procedures using primers that hybridize to the second adaptor ends. Hence, only the tester DNA fragments with second adaptor ends are amplified. Any tester DNA which hybridized with driver DNA will not be amplified. A large excess of driver DNA is used to promote formation of hybrids that are commonly found in both the tester and driver samples. The result is a second tester amplicon with fragments which were uniquely unmethylated in the original tester DNA sample.

DNA fragments cut on only one end with the master restriction enzyme ("single master-cut fragments") are eliminated by the present invention is several ways. First, only one end of those fragments will ligate to an adaptor. This means that, during any amplification step, the single master-cut fragments will not be amplified as quickly as the "double master-cut fragments" which have adaptors at both ends. As is known to the skilled artisan, fragments which hybridize with amplification primers at both ends are amplified geometrically, while DNA fragments which hybridize with amplification primers at only one end are amplified arithmetrically. Second, during the subtraction/hybridization step those single master-cut fragments may also hybridize to their driver homologues because the driver is present in vast molar excess. This imperfect hybrid can be eliminated by treatment with nuclease, so it will not be amplified during the subsequent DNA amplification step.

Several rounds of amplification and subtraction/hybridization can be used to isolate discrete DNA fragments which can be used as probes to detect hypomethylation, hypermethylation and mutation in specific regions of the genome. Discrete DNA fragments isolated by the present MDD methods which can be used to detect hypomethylation, hypermethylation and mutations in genomic DNA samples from different cell types include DNA fragments having SEQ ID NO:7–10.

While discrete DNA fragments which detect hypomethylation also frequently detect hypermethylation, the MDD method is readily adapted to permit isolation of fragments which will specifically detect hypermethylation in identified sites of the genome. This is accomplished merely by using normal cell DNA as the source of DNA for the hypermethylation probe. In this case, the normally unmethylated DNA will be cut by the methylation-sensitive master enzyme while the hypermethylated test DNA will not be cut. To eliminate DNA fragments which are common to the normal and test DNA samples, the normal cell DNA is hydridized with an excess of test cell DNA (now called "test driver DNA"). Hence, isolation of hypermethylation probes generally involves the same manipulations, as used for isolation of hypomethylation probes, but the roles of the normal cell DNA and the test cell DNA are reversed.

Also for detecting and isolating DNA fragments that have a hypermethylated CNG, a methylation-sensitive enzyme can be used as a partner enzyme and a nonmethylation sensitive enzyme as a master enzyme. When this modification is used, the adaptors are still designed to attach to the ends of DNA fragments cut by the nonmethylation sensitive master restriction enzyme.

In particular, the present invention provides a method of isolating a probe to detect hypermethylation in a CNG triplet of DNA which includes:

a) cleaving a normal sample of genomic DNA with a master restriction enzyme and a partner restriction enzyme to generate a cleaved normal sample;

b) amplifying the cleaved normal sample using primers that recognize DNA ends cut by the master restriction enzyme, to generate a first normal amplicon;

c) melting and hybridizing the first normal amplicon with a test driver DNA to generate a normal-normal product and a normal-driver product;

d) adding nucleotides to the ends of the normal-normal product and the normal-driver product to make a blunt-ended normal-normal product and a blunt-ended normal-driver product;

e) amplifying the blunt-ended normal-normal product and the blunt-ended normal-driver product by using primers which recognize only master-enzyme-cut DNA ends, to produce a second normal amplicon;

f) isolating a discrete DNA fragment from the second normal amplicon as a probe to detect the hypermethylation in a CNG triplet of DNA;

wherein the test driver DNA is cut with both the master restriction enzyme and the partner restriction enzyme, and then amplified by using primers that recognize DNA ends cut by the master restriction enzyme.

The normal sample of genomic DNA is obtained by isolating genomic DNA from a "normal" cell type, and the test driver DNA is obtained by isolating genomic DNA from a "test" cell type which may have hypermethylated DNA sites in place of the normal non-methylated DNA at that site. Here, the test cell type is a cancerous or tumorous cell type.

In a further embodiment, the present MDD techniques can be used to identify and isolate mutations in genomic DNA and it has particular utility for identifying mutations which are near the promoters or coding regions of genes. Nonmethylation-sensitive master restriction enzymes can be used for isolating mutations. However, the preferred master enzymes recognize CNG DNA sequences including CpG dinucleotides which are frequently methylated in human genome. Condensed CpG islands appear in gene promoter regions, or even in the first exons. Because CpG islands appear in gene promoter regions, and in the first few exons of many genes, MDD-identified lesions will often be close to genes which cause disease.

According to the present invention, MDD can be used to isolate probes for detecting any type of genomic lesion. For example, MDD.can be used to identify fragments which have point mutations, deletions, insertions, amplifications, rearrangements, and other mutations.

MDD is readily adapted for isolating mutations in DNA sequence by using a partner enzyme, now called a detector enzyme, that cuts normal DNA but which will not cut the mutated DNA. For example, a point mutation in tester DNA can be identified when a cleavage site recognized by the detector enzyme is eliminated. When cut with master and detector restriction enzymes, a fragment with both ends cleaved by the master enzyme will be present in the tester DNA. However, the detector enzyme cleaves this fragment in the driver DNA, because normal DNA has no point mutation. As a result, the fragment containing the point mutation will be isolated after performing the present MDD amplification and subtraction/hybridization steps. The point mutation can be easily identified by comparing the DNA sequence of the isolated mutant fragment with the DNA sequence of the homologue isolated from a matched normal genomic DNA. Moreover, the mutant tester fragment will contain the entire mutation—rather than just part of the mutation as would occur if a detector enzyme were used that cut the mutation rather than the normal DNA site.

Similarly, MDD is readily adapted for isolating deletion mutations in DNA ismply by using tester DNA as the driver DNA and normal DNA as the source of the intact fragment whose homologue in the tester DNA has a deletion. The deletion mutant fragment can be isolated by virtue of its partial homology with the normal DNA fragment.

In particular, the present invention provides a method of identifying a probe to detect a mutation in a tester sample of genomic DNA which includes:

a) cleaving a tester sample of genomic DNA with both a master restriction enzyme and a detector restriction enzyme to generate a cleaved tester sample;

b) ligating a first set of adaptors onto master enzyme cut DNA ends of the cleaved tester sample to generate a first-tester amplification template;

c) amplifying the first-tester amplification template to generate a first-tester amplicon by in vitro DNA amplification using primers that hybridize to the first set of adaptors;

d) cleaving off the first adaptors from the first-tester amplicon and ligating a second set of adaptors onto DNA ends of the first-tester amplicon to generate a second-adaptor-tester which has second adaptor ends;

e) melting and hybridizing the second-adaptor-tester with about a 10-fold to about a 10,000-fold molar excess of a driver DNA to generate a mixture of tester—tester product and tester-driver product;

f) adding nucleotides onto DNA ends present in the mixture to make a blunt-ended tester—tester product and a blunt-ended tester-driver product;

g) amplifying the blunt-ended tester—tester product and the blunt-ended tester-driver product by in vitro DNA amplification using primers that hybridize to second adaptor ends to generate a second-tester amplicon;

h) isolating a discrete DNA fragment from the second tester amplicon as a probe to detect a mutation in the tester sample of genomic DNA;

wherein the detector restriction enzyme cleaves a normal DNA site but a mutant DNA site to produce DNA fragments with a complexity of about 5% to about 25% of the genomic DNA in a size range which can be amplified by a DNA amplification enzyme; and wherein the driver DNA is cut with both the master restriction enzyme and the detector restriction enzyme and amplified using primers that recognize DNA ends cut by the master restriction enzyme.

Probes isolated by the present MDD techniques have at least about 14 nucleotides to about 2000 nucleotides.

For identifying mutations and isolating DNA fragments containing those mutations, selection of a detector restriction enzyme involves identifying an enzyme which will not cut mutated genomic DNA but which will cut normal DNA. The skilled artisan can readily perform this analysis, for example, by testing a plurality of restriction enzymes in the present MDD methods.

According to the present invention, a mutation, hypomethylation and hypermethylation at a specific site in genomic DNA can be detected by observing whether the size or intensity of a DNA fragment cut with a master or detector restriction enzyme is the same in control and test samples. This can be done by cutting genomic DNA isolated from control and test tissue samples with the master or detector restriction enzyme, hybridizing a probe to the control and test DNAs and observing whether the two hybridization complexes are the same or different sizes or intensities.

In particular, the present invention provides a method of detecting whether a CNG triplet is hypomethylated or hypermethylated in a genomic DNA present in a test sample of cells which includes:

a) isolating genomic DNA from a control sample of cells and a test sample of cells to generate a control-cell DNA and a test-cell DNA;

b) cleaving the control-cell DNA and the test-cell DNA with a master restriction enzyme to generate cleaved control-cell DNA and cleaved test-cell DNA;

c) preparing a probe from a DNA isolated by the methods of the present invention, for example, a DNA selected from the group consisting of SEQ ID NO:7–10;

d) hybridizing the probe to the cleaved control-cell DNA and the cleaved test-cell DNA to form a control-hydridization complex and a test-hybridization complex; and e) observing whether the size of the control-hydridization complex is the same as the size of the test-hybridization complex.

Similarly, the present invention provides a method of detecting whether a DNA site is mutated in a genomic DNA present in a test sample of cells which includes:

a) isolating genomic DNA from a control sample of cells and a test sample of cells to generate a control-cell DNA and a test-cell DNA;

b) cleaving the control-cell DNA and the test-cell DNA with a detector restriction enzyme to generate cleaved control-cell DNA and cleaved test-cell DNA;

c) preparing a probe from a discret DNA isolated by the methods of the present invention;

d) hybridizing the probe to the cleaved control-cell DNA and the cleaved test-cell DNA to form a control-hydridization complex and a test-hybridization complex; and e) observing whether the size of the control-hydridization complex is the same as the size of the test-hybridization complex;

wherein the detector restriction enzyme does not cleave a mutated DNA site but does cleave a corresponding nonmutated DNA site.

Hybridization techniques for detecting specific genomic DNA fragments are known in the and include solid-phase-based hybridization and solution hybridization which use any of the known reporter molecules. Detailed methodology for gel electrophoretic and nucleic acid hybridization techniques can be found in Sambrook et al.

Preferred nucleic acid probes for detecting hypomethylation and hypermethylation have SEQ ID NOS:7–10.

According to the present invention, a probe isolated by the subject methods, can be labelled by any procedure known in the art, for example by incorporation of nucleotides linked to a "reporter molecule".

A "reporter molecule", as used herein, is a molecule which provides an analytically identifiable signal allowing detection of a hybridized probe. Detection may be either qualitative or quantitative. Commonly used reporter molecules include fluorophores, enzymes, biotin, chemiluminescent molecules, bioluminescent molecules, digoxigenin, avidin, streptavidin or radioisotopes. Commonly used enzymes include horseradish peroxidase, alkaline phosphatase, glucose oxidase and β-galactosidase, among others. Enzymes can be conjugated to avidin or streptavidin for use with a biotinylated probe. Similarly, probes can be conjugated to avidin or streptavidin for use with a biotinylated enzyme. The substrates to be used with these enzymes are generally chosen for the production, upon hydrolysis by the corresponding enzyme, of a detectable color change. For example, p-nitrophenyl phosphate is suitable for use with alkaline phosphatase reporter molecules; for horseradish peroxidase, 1,2-phenylenediamine, 5-aminosalicylic acid or tolidine are commonly used.

Incorporation of a reporter molecule into a DNA probe can be by any method known to the skilled artisan, for example by nick translation, primer extension, random oligo priming, by 3' or 5' end labeling or by other means (see, for example, Sambrook et al.).

In another embodiment, the present invention provides one or more compartmentalized kits for detection of hypomethylation. A first kit has a receptacle containing at least one of the present isolated probes. Such a probe may be a nucleic acid fragment which is methylated at a CNG trinucleotide in the genomic DNA of normal cells but which not methylated in the genomic DNA of cancerous cells. Such a probe may be specific for a DNA site that is normally methylated but which is nonmethylated in certain cell types. Similarly, such a probe may be specific for a DNA site that is abnormally methylated or hypermethylated in certain cell types. Finally, such a probe may identify a specific DNA mutation. The probe provided in the present kits may have a covalently attached reporter molecule.

A second kit has at least one receptacle containing a reagent for MDD. Such a reagent can be, for example, a preferred master restriction enzyme, a preferred partner restriction enzyme, a preferred adaptor which can be ligated to DNA cut with the preferred master restriction enzyme, a primer that hybridizes to a preferred adaptor, and the like.

Using the MDD methods of the present invention, several methyl-polymorphic markers or sites in the human genome have been identified and DNA fragments encoding these marker sites have been isolated from different cell types. In particular, the present MDD methods have been used to identify hypomethylated sites which act as markers indicating whether a patient has cancer. These sites were identified using B-cells from patients with Chronic Lymphocytic Leukemia (CLL) and using tumor cells from breast cancer patients.

Moreover, for the first time the present methods and probes experimentally prove that methylated external cytosine at CpCpG triplet sequences do exist in the human genome, and that alteration of their methylation patterns is related to human cancer development. According to the present invention, methylation of the first base of CpCpG triplets is not a random event. Instead, it is a site- and tissue-specific event.

The alteration of the methylation pattern in CpCpG triplets may be a key, and common event, in the development of neoplasia. Imbalanced methylation at CpCpG triplet may play at least two roles in tumorigenesis:

1) DNA hypomethylation may cause some proto-oncogene expression or DNA hypermethylation may silence a tumor supressor which contributes to neoplastic growth; and 2) DNA hypomethylation may change chromatin structure, and induce abnormalities in chromosome pairing and disjunction. Such structural abnormalities may result in genomic lesions, such as chromosome deletions, amplifications, inversions, mutations, and translocations, all of which are found in human genetic diseases and cancer.

Hence, the present MDD methods have broad utility for identifying differentially methylated sites at CpCpG triplet sequences in the human genome; for mapping hypo- and hyper-methylation sites which are related to disease development; for understanding the role(s) of DNA methylation in normal cell genomic DNA imprinting, differentiation, and development; for understanding tumorigenesis; for diagnosing and monitoring the prognosis of disease; and for searching for proto-oncogene(s) and recessive oncogene(s). MDD, as a comprehensive molecular genetic technique, enables the accumulation of knowledge necessary to help better understand the etiology of human genetic diseases and cancer.

The following examples further illustrate the invention.

EXAMPLE 1

Materials and Methods

Figure 1B:
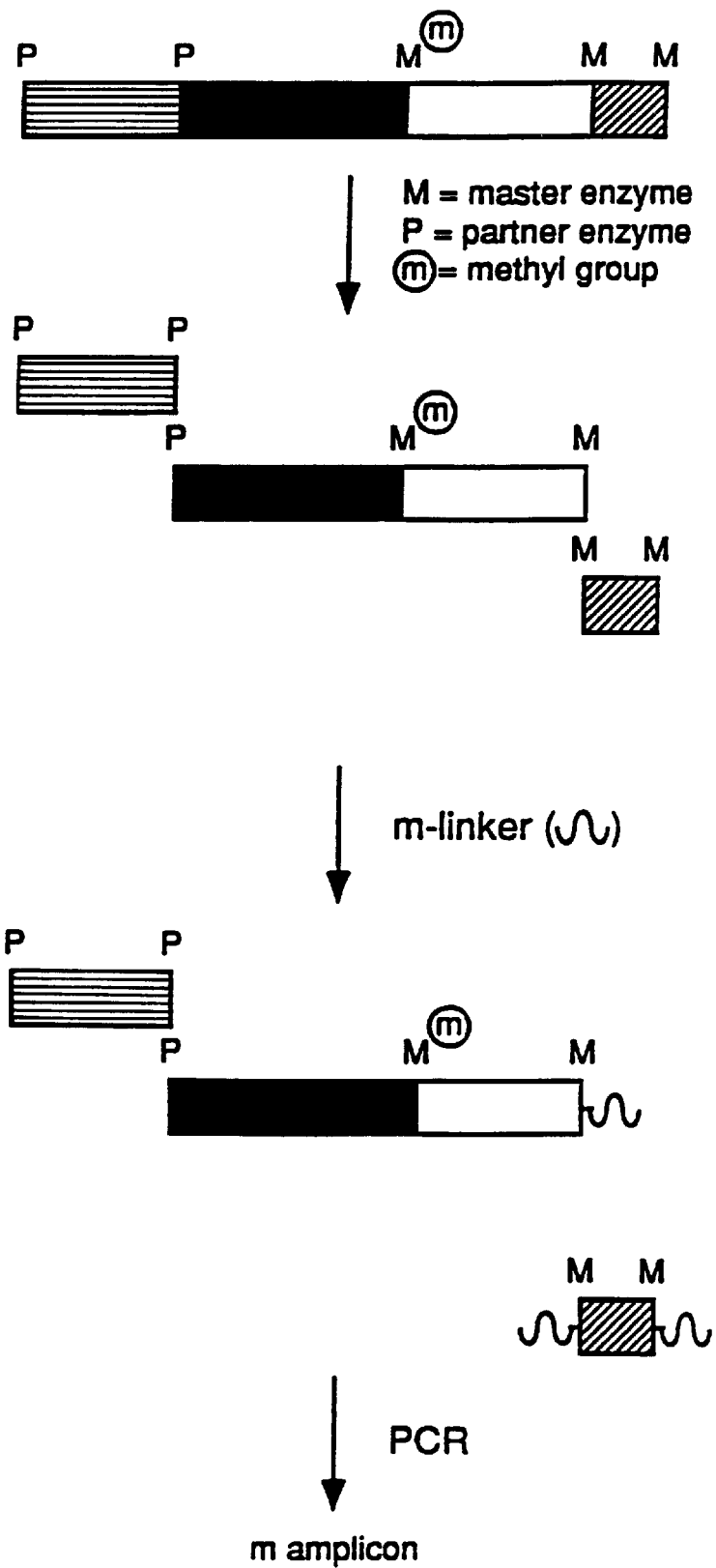

To test the MDD technique, a working model system was designed to isolate methyl-polymorphic DNA markers (see FIG. 1 for a schematic diagram of the MDD methods). There is evidence that in mammalian DNA, methylation patterns are both tissue-, and cell-type specific. Hence, DNA was isolated from two different types of cells from patients who have chronic lymphocytic leukemia (CLL). In CLL patients, the number of $CD5^+$ B type lymphocytes is abnormally high. These $CD5^+$ cells can be isolated by highly specific antibodies in a fluorescence activated cell sorter (FACs). For performing MDD, the DNA isolated from these $CD5^+$ cells served as the tester, while DNA isolated from neutrophils of the same patient served as the driver. A methyl-polymorphic DNA probe, named CLL58, which exhibited methyl-differential displays was isolated from an individual CLL patient.

After the successful isolation of these methyl-polymorphic probes, MDD was again successfully used in the isolation of methylpolymorphic probes from breast cancer biopsies. Three methyl-polymorphic probes, BR50, BR104, and BR254, which gave methyl-differential displays in breast cancer and their matched normal cells, were isolated from three individual patients. BR50 and BR254 also gave methyl-differential displays in ovarian cancer and their matched normal cells, while the BR254 probe exhibited a methyl-differential display in colon cancer cells.

DNA Isolation from malignant B-cells and neutrophil cells. Mononuclear and neutrophil cells were isolated from the peripheral whole blood of CLL patients by Ficoll/Hypage centrifugation. Leukemic B-cells ($CD5^+$), were sorted from mononuclear cells in the presence of fluorescent anti-CD5 antibodies by FACs. DNAs were isolated by the phenol extraction method. Sambrook, J., Fritsch, E. F. and Manitis, T., (1989) Molecular Cloning, 9.16–9.19.

DNA from human cancer biopsies. Dissected human breast, ovarian, and colon cancer tissues (tumor and normal) were immediately frozen in liquid nitrogen, and stored at –70° C. DNAs were isolated from both tumor and matched normal tissues by the phenol extraction method. Sambrook, J., Fritsch, E. F. and Manitis, T., (1989) Molecular Cloning, 9.16–9.19.

MDD. To prepare tester and driver amplicons, 1–2 μg of tester and driver genomic DNA were digested simultaneously with Msp I and MseI restriction endonucleases (New England Biolabs). The digested DNAs were extracted with phenol/chloroform once, and precipitated with 2 volumes of ethanol after adding ¹⁄₁₀ volume of 3M NaAc.

The DNAs were then resuspended in 10 μl of TE buffer (10 mM Tris.HCl, 0.1 mM EDTA, pH8.0). To ligate the first pair of oligonucleotide adapters (MSA24 with SEQ ID NO:1 and MSA12 with SEQ ID NO:2) to the digested tester and driver amplicon DNAs, 10 μl (1 μg) of digested DNA was mixed with: 2.5 μl of each of the unphosphorylated single strand adapters having SEQ ID NO:1 (0.6 μg/μl) and SEQ ID NO:2 (0.3 μg/μl); 2 μl of 10× ligation buffer (Boehringer Mannheim); and 3 μl of $ddH_2O$. The oligonucleotide adapters were annealed by cooling the mix gradually from 55° C. to 10° C. over a 1.5 hour period in a 4° C. cold room, and then ligated to MspI/MseI-cut DNA fragments by overnight incubation with 1 U of T4 DNA ligase (Boehringer Mannheim) at 16° C. After ligation, the ligate was diluted with TEt buffer (10 mM Tris.HCl, 0.1 mM EDTA, 20 μg/ml of tRNA) at a concentration of 2 μg/μl.

To generate the tester and driver amplicons, tester and driver DNA ligated to the first set adapters were separately amplified by polymerase chain reaction ("PCR"). Two PCR tubes were set up to make the tester amplicon, while five PCR tubes were prepared for the driver amplicon. Each tube has a 400 μl reaction mixture containing 67 mM Tris-HCl, pH 8.8 at 25° C., 4 mM $MgCl_2$, 16 mM $(NH_4)_2SO_4$, 10 mM β-mercaptoethanol, 100 μg/ml of non-acethylated bovine serum albumin, 24 μl of dNTP (5 mM for each dATP, dCTP, dGTP, and dTTP), 8 μl of SEQ ID NO:1 (0.6 μg/μl), and 80 ng of DNA ligated to the adapters as templates. While the tubes were equilibrated at 72° C. in a thermal cycler (Perkin-Elmer Cetus), 12U of Taq DNA polymerase (Perkin-Elmer Cetus), and 3U of pwo DNA polymerase (Boehringer Mannheim) were added. The reaction was overlaid with mineral oil and incubated for 5 minutes to fill-in the 3'-recessed ends of the ligates, and the DNAs were then amplified by 24 cycles of PCR. Each PCR cycle included 1 minute at 95° C., 1 minute at 67° C. and 3 minutes at 72° C., and the last cycle was followed with a 10 minute extension time at 72° C. The DNA amplicons were extracted once with phenol, once with phenol/chloroform, and precipitated by 2 volumes of 100% ethanol after adding ¼ volume of 10M $NH_4Ac$. Amplicon DNAs were then resuspended in TE buffer.

To remove the first set of adapters from the driver amplicon, 80 μg of driver amplicon DNA was digested to completion with Msp I enzyme (10U/μg). The driver amplicon DNA was extracted once with phenol/chloroform, and after adding ¼ volume of 10M $NH_4Ac$, the DNA was precipitated with 2 volumes of 100% ethanol. The amplicon DNA was resuspended in TE buffer at a concentration of 0.5 μg/μl. To change the tester amplicon DNA adapters, 5 μg of tester amplicon was digested with Msp I (10U/μg). The digested tester amplicon DNA was purified by PCR purification spin column (Boehringer Mannheim).

For the hybridization/subtraction and amplification steps, Msp I digested tester amplicon DNA was ligated to a second set of adapters (MSB24 having SEQ ID NO:3 and MSB12 having SEQ ID NO:4): 1 μl (0.2 μg) of digested tester DNA was mixed with 1 μl of the SEQ ID NO:3 adaptor (0.6 μg/μl), 1 μl of the SEQ ID NO:4 adaptor (0.3 μg/μl), 1 μl of 10× ligation buffer, and 6 μl of $ddH_2O$. The same annealing and ligation steps were performed as for ligation of the first set of adapters. After ligation, the ligate was diluted with 40 μl of TEt buffer and mixed with 20 μg (40 μl) of driver amplicon DNA. The mix was extracted with phenol/chloroform once, and precipitated by adding ¼ volume of 10M $NH_4Ac$, and 2.5 volumes of 100% ethanol in a dry ice/ethanol bath for 10 minutes. The reaction solution was equilibrated to room temperature and the DNA was collected by centrifugation. The pellet was washed twice with 70% ice cold ethanol, dried, resuspended in 2 μl of 3×EE buffer. D. Straus et al., 87 Proc. Natl. Acad. Sci. USA. 1889 (1990). After resuspension, the DNA was overlaid with one drop of mineral oil (Perkin-Elmer Cetus), denatured at 100° C. for 5 minutes, and 0.5 μl of 5M NaCl was added. The DNAs were hybridized at 68° C. for at least 20 hours.

To amplify the difference products (DP1), the 3'-recessed ends were first filled in with DNA polymerase. The hybridized product was diluted with 198 μl of TE buffer, and a 50 μl of filling-in reaction was set up: 30 μl of diluted DNA hybrids, 10 μl of 5× PCR buffer, 2 μl of dNTP (5 mM for each dATP, dCTP, dGTP, and dTTP), and 8 μl of ddH$_2$O. The reaction was equilibrated at 72° C., 3U of Taq DNA polymerase (Perkin-Elmer Cetus) and 0.75U of pwo DNA polymerase (Boehringer Mannheim) were added at 72° C. for 10 minutes. The filled-in DNA hybrids were purified by a PCR purification spin column (Boehringer Mannheim).

To reduce the background for DP1 amplification, mung bean nuclease treatment of the filled-in DNA hybrids was performed: 9 μl of filled-in DNA hybrid solution mixed with 1 μl of 10× mung bean nuclease reaction buffer and 50U of mung bean nuclease (Boehringer Mannheim) was incubated at 30° C. for 30 minutes. The reaction was terminated by heat inactivation at 100° C. for 5 minutes after adding 40 μl of 50 mM Tris-HCl (pH 8.9).

To amplify DP1, 1 tube of 100 μl PCR reaction was set up. The reaction consisted of 20 μl of mung bean nuclease-treated DNA hybrid solution, 20 μl of 5×PCR buffer, 5 μl of dNTP (5 mM for each dATP, dCTP, dGTP. and dTTP), 2 μl of the SEQ ID NO:3 adaptor, and 52 μl of ddH$_2$O. The reaction was hot started at 94° C. for 2 minutes after adding 3U of Taq DNA polymerase (Perkin-Elmer Cetus) and 0.75U of pwo DNA polymerase (Boehringer Mannheim). The conditions for the PCR were 1 minute at 95° C., 1 minute at 67° C., and 3 minutes at 72° C. for 35–40 cycles. The last cycle was followed with a 10 minutes extension step at 72° C. The DP1 was purified by PCR purification spin column (Boehringer Mannhein), and the concentration of the DNA was determined at O.D.$_{260}$ in a spectrophotometer.

To prepare the second round of hybridization/subtraction and amplification steps, 3 μg of DP1 was digested with the restriction endonuclease Msp I (10U/μg) in a 30 μl reaction. The digested DP1 was purified with PCR purification spin column (Beohringer Mannheim).

To put a new set of adapters (MSC24 having SEQ ID NO:5 and MSC12 having SEQ ID NO:6) on DP1, 2 μl (0.1 μg) of DP1 was mixed with 1 μl of the SEQ ID NO:5 adaptor (0.6 μg/μl), 1 μl of the SEQ ID NO:6 adaptor (0.3 μg/μl), 1 μl of 10× ligation buffer (Beohringer Mannheim), and 6 μl of ddH$_2$O. The annealing and ligation reactions were done as before. The ligate was diluted with 40 μl of TEt buffer to the concentration of 2 ng/μl.

To set up the hybridization reaction, 20 ng (10 μl) of diluted ligate was mixed with 20 μg (40 μl) of driver amplicon DNA. The DNA mix was extracted with an equal volume of phenol/chloroform once, and precipitated with 2.5 volumes of 100% ethanol after adding ¼ volume of 10M of NH$_4$Ac in a dry ice/ethanol bath for 10 minutes. The reaction solution was equilibrated to room temperature and the DNA was collected by centrifugation. The pellet was washed twice with 70% ice cold ethanol, dried, and resuspended in 2 μl of 3×EE. 0.5 μl of 5M NaCl was added after the DNA mix was denatured at 100° C. for 5 minutes. The hybridization reaction-was carried out at 68° C. for a minimum period of 20 hours.

To amplify the secondary different product (DP2), the hybrids were diluted with 198 μl of TE buffer, and 100 μl of PCR amplification reaction was set up as follows: 4μl of the diluted hybrid solution, 5 μl of dNTP (5 mM for each dATP, dCTP,dGTP, dTTP), 20 μl of 5× PCR reaction buffer, and 69 μl of ddH$_2$O. While the PCR tube was equilibrated at 72° C., 3U of Taq DNA polymerase (Perkin-Elmer Cetus) and 0.75U of pwo DNA polymerase (Boehringer Mannheim) were added to fill-in the 3'-recessed ends for 10 minutes. 2 μl of the SEQ ID NO:5 adaptor (0.6 μg/μl) was then added. The PCR reaction was hot started by raising the temperature to 94° C. for 2 minutes, and 35 to 40 cycles of PCR reaction were performed under the same conditions as were used for amplifying DP1.

DP2 usually contained several individual DNA fragments when electrophoresed on a 2% agarose gel. The individual DNA fragments were purified by DNA gel extraction kit (Qiagen Inc.), and subcloned into pUC118 vector, which was linearized by the restriction endonuclease AccI. If the DP2 product had some DNA smear, it was treated with mung bean nuclease as described above.

For each MDD, twelve to twenty colonies were chosen to amplify their inserts, from which different sized probes were selected for amplicon Southern Blotting, and human genomic DNA Southern Blotting.

Amplicon DNA Southern Blot. The first round of positive probe screening was performed with amplicon DNA Southern Blots. Non-Radiation Southern Blot and Detection Kits (GENIUS™) were purchased from Boehringer Mannheim. Probe labeling, and detection followed the instruction of the manufacturer.

Two to three μg of tester and driver amplicon DNA were electrophoresed on a 2% agarose gel, and blotted to positively charged nylon membranes (Boehringer Mannheim). For prehybridization, the membranes were placed at 68° C. for 2–4 hours in solutions containing 6×SSC, 5× Denhardt's solution, 0.5% SDS, 0.1M EDTA, and 50 μg/ml of salmon sperm DNA. Under the same conditions, the probes were added, and hybridized to the membranes overnight. The membranes were then rinsed three times with 2× SSC, 1×blot wash (12 mM Na2HP04, 8 mM NaH2PO4, 1.4 mM Na4P207, 0.5% SDS) at 68° C., and further washed three times (30 minutes for each time) with the same buffer at 68° C. Next, the membranes were equilibrated in buffer A (100 mM Tris.HCl, 150 mM, pH 7.5) and transferred into buffer B (2% black reagent in buffer A) solution and incubated at room temperature for one hour. The membranes were then washed 2 times (15 minutes for each time) with buffer A, and equilibrated in buffer C (100 mM Tris.HCl, 100 mM NaCl, 10MM MgCl2). Before the membranes were exposed on Kodak X-OMAT film, they were rinsed in lumi-P530 for 1 min and kept in a plastic sheet protector. Positive clones were identified by observing the probe hybridized more heavily to test amplicon DNA than to driver amplicon DNA.

Human Genomic DNA Southern Blot. The positive probes that were confirmed by the amplicon DNA Southern Blot experiment were tested further by human genomic DNA Southern Blotting. Genomic DNAs isolated from cancer tissues, and their respective matched normal tissues, were digested with Msp I restriction endonuclease, electrophoresed on 1.5% agarose gels, and transferred to Hybond Membranes (Amersham, Arlington Heights, Ill.). These membranes were exposed to UV light to immobilize the DNA. The probes for the Southern Blot were labeled with High Prime DNA labeling kits (Boehringer Mannheim) following the instructions of the manufacturer. The procedure for hybridization and blot wash were the same as in the Amplicon DNA Southern Blotting section.

EXAMPLE 2

Figure 2:
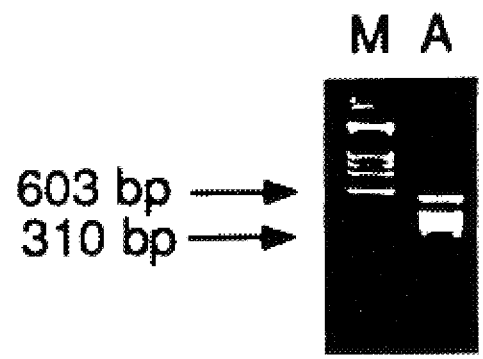

Different Methylation Patterns at CpCpG Sites in Malignant B-cells and Neutrophil Cells DNA isolated from malignant B-cells and neutrophil cells of four CLL patients (#58, #111, #112, #128) was used to perform MDD as described above in the Materials and Methods provided in Example 1. The DNA from leukemic B-cells was used as the tester, and the DNA from neutrophil cells was used as the driver. Tester and driver DNAs were simultaneously digested with the restriction endonucleases, Msp I and Mse 1. After ligating the first set of adapters to the digested tester and driver DNA fragments, tester and driver amplicons were generated by PCR amplification (see Materials and Methods). After two rounds of hybridization/ subtraction and amplification, the different products (DP2) which were isolated from patient 111 appeared as individual DNA fragment bands on an agarose gel (FIG. 2). The DP2 fragments were then subcloned into the plasmid pUC118 (see Materials and Methods), and amplified by PCR. For the first round of selection, inserts of different sizes were selected and hybridized to the tester and driver amplicon DNAs from which they were derived in a non-radioactive Southern Blot experiment (see materials and methods). The positive probes were selected if they hybridized a single band in the tester amplicon only, or if they hybridized to both tester and driver amplicon DNA, but the hybridization to the driver amplicon DNA band was far less intense. The final proof of a positive probe was that it displayed a different methylation pattern in a genomic DNA Southern Blot experiment in which the parental malignant B-cell, and normal neutrophil cell genomic DNA, were digested with the restriction endonuclease Msp I (see materials and methods).

Figure 3:
Figure 3:

The CLL58 probe isolated from patient #111 fulfilled these requirements. When CLL58 was hybridized to its tester and driver amplicon DNA, the tester amplicon DNA gave a heavy hybridization band, while the driver amplicon DNA gave a much less intense hybridized band (FIG. 3).

Figure 4:
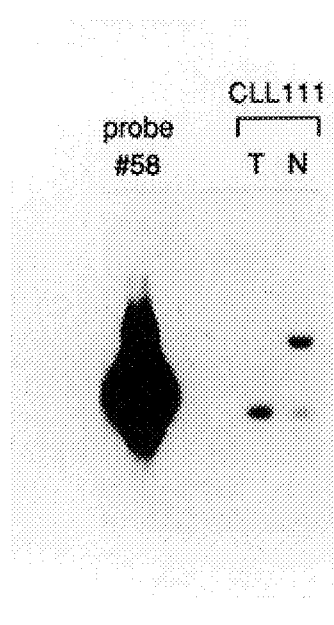

The CLL58 probe was further tested by hybridization to a genomic Southern blot of MspI-digested malignant B-cell and neutrophil cell DNA. The genomic Southern Blot revealed that a larger fragment was much less intensely hybridized than a lower molecular weight fragment in the malignant B-cell DNA, while in the neutrophil cell DNA, just the opposite result occurred (FIG. 4). These results demonstrate that in human genomic DNA, there are methylated external cytosine residues at CpCpG sequences, and those CpCpG sequences are differentially methylated in different types of cells. Moreover, the CLL58 probe can detect and distinguish cell-type specific methylation patterns.

EXAMPLE 3

MDD-Isolated Probes from Human Breast Cancer Tumors Also Detect Ovarian and Colon Cancers We have proven the existence of methylation of the external cytosine residue at CpCpG sites in the human genome, and have isolated CpCpG site related methylpolymorphic markers in a working model system. MDD was then applied to successfully isolate CpCpG related methylpolymorphic markers from human breast cancer biopsies.

Isolation of Probes From Breast Tumor DNA

Figure 5:
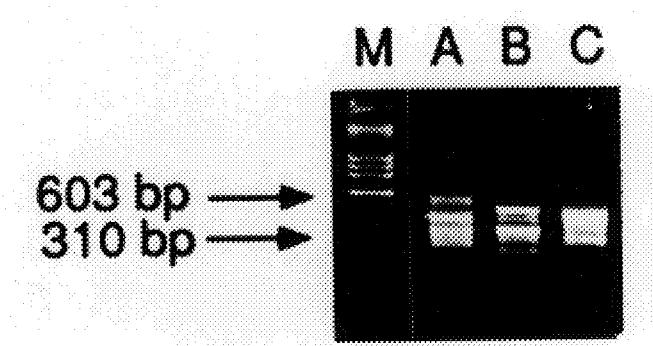

MDD was used to test five pairs of DNA samples (tumor DNA and matched normal DNA) obtained from five breast cancer patients. To isolate methyl-polymorphic markers, tumor DNA served as the tester, and normal DNA served as the driver. MDD was performed in the same manner as described in Example 1. Individual DNA fragments were isolated by MDD from three breast cancer patients after two rounds of hybridization/subtraction and amplification (FIG. 5).

Figure 6A:
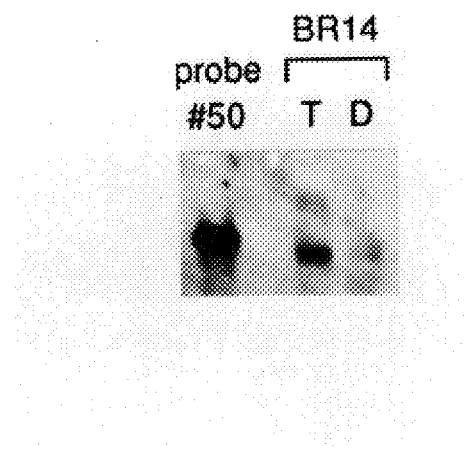
Figure 6B:
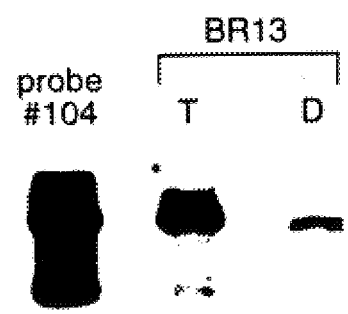
Figure 6C:
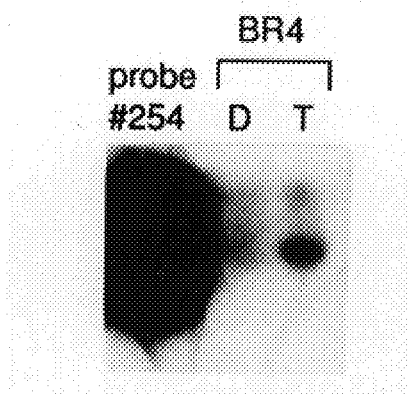

Three probes were further analyzed, BR50, BR104, and BR254, isolated from patient #14, patient #13, and patient #4, respectively. Each of these three probes appropriately hybridized with their own tester amplicon DNA, but also hybridized slightly with the driver amplicon DNA (FIG. 6a–c).

Figure 7A:
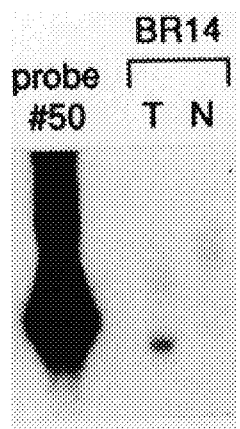

These probes were then examined further by hybridizing them to MspI-digested parental tumor and matched normal genomic DNAs. The genomic Southern Blot for probe BR50 showed that the probe hybridized with a lower band to a much greater degree than to an upper band in tumor DNA (FIG. 7a). However, in normal DNA, just the opposite occurred—the BR50 probe hybridized to the upper band more than to the lower band (FIG. 7a).

Figure 7B:
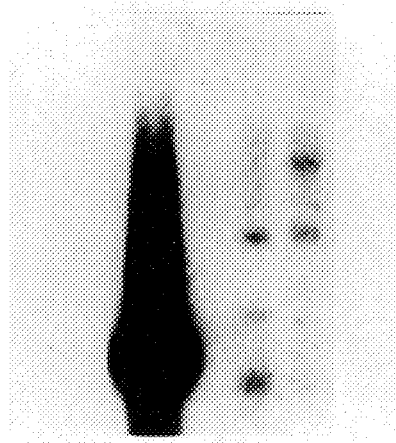

The genomic DNA Southern Blot for probe BR104 showed that the probe hybridized with a lower and a middle band in the tumor DNA, while in the normal DNA, probe BR104 hybridized with a middle and an upper band (FIG. 7b).

Figure 7C:
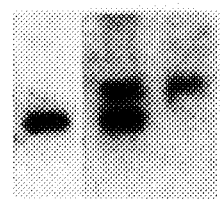

For the probe BR254, the Southern Blot result showed that it hybridized with a lower band and a upper band in the tumor DNA, however, it only hybridized with an upper band in the normal DNA (FIG. 7c).

The results of three cases, indicate that in normal cells the genomic DNA is more highly methylated, is cut less frequently and gives rise to larger fragments than is observed for DNA from tumor cells. The isolated probes therefore hybridize to higher molecular weight bands in normal DNA. In contrast, the lower bands which were hybridized with probes BR50, BR104, and BR254, are generated by demethylation of the external C residue at CpCpG DNA sites in the tumor cells. The weakly hybridized upper bands in the tumor DNA are likely caused by normal cell contamination.

Breast Tumor Probes Detect Hypomethylation in Other Cancer Patients

Figure 8:
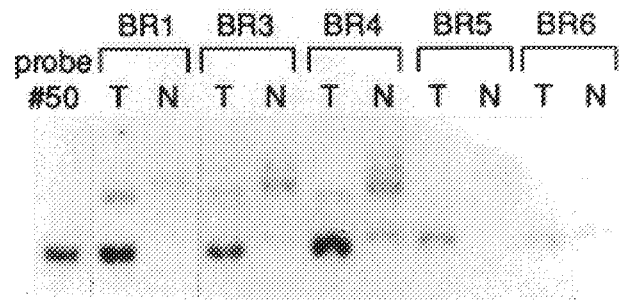
Figure 9:
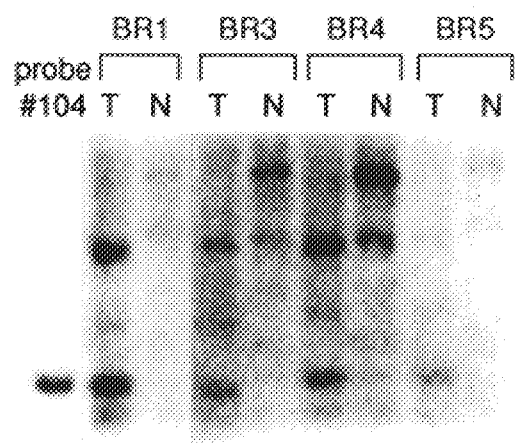

To understand whether this hypomethylation event also happens in other breast cancer patients, normal cell and tumor cell DNA was isolated from ten breast cancer patients, cleaved by the Msp I enzyme, and probed with BR50 and BR104. Of the ten breast patients whose DNA was probed with BR50, five had a hybridization pattern which was similar to that of the patient from which BR50 was isolated (the "parental patient") (FIG. 8). Of the ten breast patients whose DNA was probed with BR104, five had a hybridization pattern similar to that of the parental patient. (See FIG. 9, providing four of these five patterns).

Figure 10:
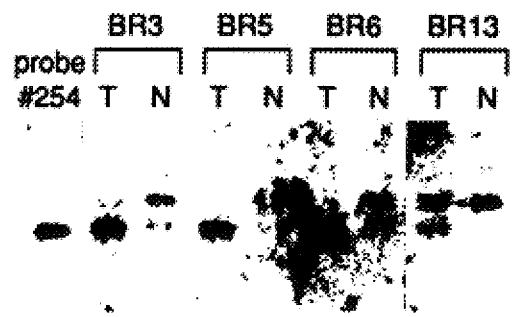

The BR254 probe was hybridized to normal and tumor DNA of 16 breast cancer patients. Of the 16 patients, 10 had a hybridization pattern which was similar to that of the parental patient. However, some differences in the methylation patterns of these patients were observed. Some patients only had the lower band in their tumor DNA, and the upper band in their normal DNA. (FIG. 10) However, other patients had the lower band in their tumor DNA, but had both lower and upper bands in their normal DNA (FIG. 10). These results indicate that the external cytosine residue at CpCpG sites are fully demethylated in some breast tumors. However, the lower bands appearing in normal DNAs probably were caused by a partial demethylation event, which suggests that the normal cells were under the process of neoplastic change. In general, the different extent of demethylation identified by probes BR50, BR104, and BR254 in human breast cancer patients is a common phenomena and may be used to predict the extent of neoplastic change.

Figure 11:

Detection of a DNA Amplification Event in a Breast Cancer Patient The BR254 probe detected a highly amplified DNA event in one of the 16 breast cancer patients tested with that probe (FIG. 11). This result provides evidence that imbalanced DNA methylation may cause a conformational change of chromatin which then induces a DNA amplification.

Hypomethylation Detection by BR50, BR104, and BR254 in Ovarian Cancers. To examine whether the same hypomethylation phenomena also happens in human ovarian cancer, DNA samples isolated from 8 patients with ovarian cancer were analyzed. For some patients, two DNA samples were obtained, one from primary ovarian cancer tissue, and the other from their matched normal tissue. For other patients, three DNA samples were obtained, they were from primary ovarian cancer tissue, metastatic tumor tissue, and matched normal tissue. The DNAs were cleaved with MspI, and hybridized with the probes BR50 and BR104 in Southern Blot experiments.

Figure 12:
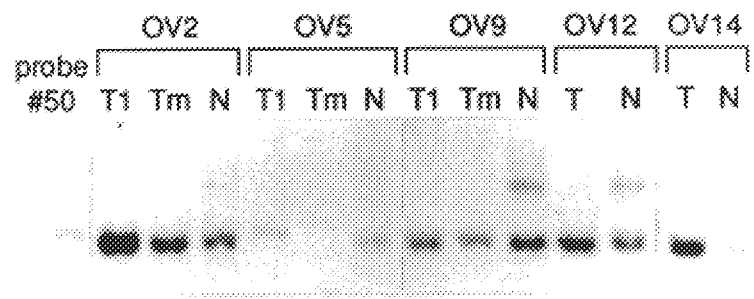

Of the eight ovarian patients tested with the BR50 probe, five patients had similar hybridization patterns: the BR50 probe hybridized almost equally to lower and upper bands in their normal DNA samples, while in the primary tumor DNA, the upper band was only slightly hybridized. Hoever, in the metastatic tumor DNA of these 5 patients, only the lower band was hybridized (FIG. 12).

No different hybridization patterns were detected using the probe BR104. This result indicates that the BR104 probe was detecting a tissue-specific hypomethylation event.

Figure 13:
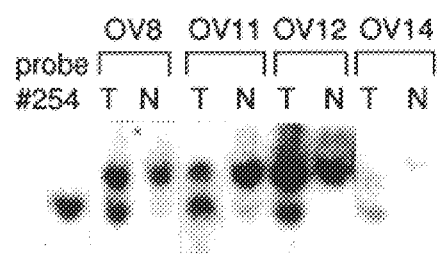

Eleven patients' DNA samples were examined using the BR254 probe. The Southern Blot results showed that of 11 patients, 4 had the same hybridization patterns which appeared in the parental DNA pair (FIG. 13).

These results suggest that probes BR50 and BR254 detect tumor-related hypomethylation events in both breast and ovarian cancer cells. Interestingly, in the case of probe BR50, the complete disappearance of the upper band in the metastatic tumor DNA indicates that the extent of demethylation seems to be related to the progression of the disease.

Hypomethylation Detection using BR50, BR104, and BR254 on Colon Cancer DNA

The methylation patterns of tumor and matched normal DNA samples isolated from 10 colon cancer patients were examined using BR50, BR104, and BR254 probes. DNAs were digested by the MspI enzyme, Southern Blots prepared and the blots were hybridized with these probes.

No difference in the methylation patterns of colon tumor and normal DNAs were detected by probes BR50 and BR104 (data not shown), indicating that both probes were detecting a tissue-specific hypomethylation event in colon cells.

Figure 14:
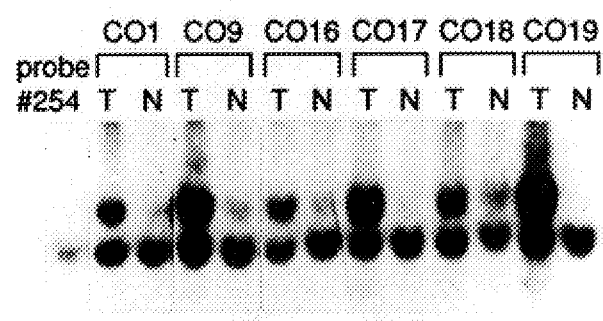

However, for the probe BR254, different methylation patterns were observed. Of the ten colon cancer patients tested, six had hypomethylation patterns opposite to those observed for the breast and ovarian cancer patients. Instead of hybridizing more to an upper band in the normal DNA samples, probe BR254 hybridized with the lower band. Moreover, instead of hybridizing more to the lower band in the tumor DNAs, BR254 hybridized equally with the lower band and a upper band (FIG. 14). These results demonstrate that while the BR254 probe detects hypomethylation in breast cancer cells, in colon cancer DNA the BR254 probe detects hypermethylation. Therefore, methylation patterns are not only tissue-type specific, but cancer-specific, and can be different in different types of cancers.

What is claimed:

1. A method of detecting whether a CNG triplet is hypomethylated or hypermethylated in a genomic DNA present in a mammalian test sample of cells which comprises:
   a) cleaving genomic DNA isolated from a control sample of cells and a test sample of cells with a master restriction enzyme to generate a cleaved control-cell DNA and a cleaved test-cell DNA;
   b) hybridizing a probe to said cleaved control-cell DNA and said cleaved test-cell DNA to form a control-hybridization complex and a test-hybridization complex, wherein said probe comprises a nucleic acid fragment which is methylated in said control sample of cells but which is not methylated in said test sample of cells; and
   c) determining whether the size of the control-hydridization complex is the same as the size of the test-hybridization complex;
   wherein said master restriction enzyme cleaves a nonmethylated CNG DNA sequence but does not cleave a methylated CNG triplet sequence.

2. The method of claim 1 wherein said nucleic acid fragment is cut by said master restriction enzyme in genomic DNA from said control sample of cells but which not cut by said master restriction enzyme in genomic DNA said mammalian test sample of cells.

3. The method of claim 1 wherein said probe comprises a DNA selected from the group consisting of SEQ ID NO:7–10.

4. The method of claim 1 wherein said master restriction enzyme is MspI, BsiSI or Hin2I.

5. The method of claim 1 wherein said mammalian test sample of cells comprises cancerous cells.

6. The method of claim 5 wherein said cancerous cells are isolated from a person with Wilms' cancer, breast cancer, ovarian cancer, colon cancer, kidney cell cancer, liver cell cancer, lung cancer, leukemia, rhabdomyosarcoma, sarcoma, or hepatoblastoma.

7. The method of claim 1 wherein said control sample of cells comprises non-cancerous cells derived from the same person as said mammalian test sample of cells.

8. The method of claim 1 wherein said control sample of cells comprises non-cancerous cells derived from the same tissue-type as said mammalian test sample of cells.

9. A method of isolating a probe to detect hypomethylation in a CNG triplet of DNA which comprises:
   a) cleaving a tester sample of genomic DNA with a master restriction enzyme and a partner restriction enzyme to generate a cleaved tester sample;
   b) amplifying said cleaved tester sample using primers that recognize DNA ends cut by said master restriction enzyme, to generate a first tester amplicon;
   c) melting and hybridizing said first test amplicon with a driver DNA to generate a tester—tester hybrid and a tester-driver hybrid;
   d) adding nucleotides to the ends of said tester—tester hybrid and said tester-driver hybrid to make a blunt-ended tester—tester hybrid and a blunt-ended tester-driver hybrid;
   e) amplifying said blunt-ended tester—tester hybrid and said blunt-ended tester-driver hybrid by using primers which recognize only master-enzyme-cut DNA ends, to produce a second tester amplicon;
   f) isolating a DNA fragment from said second tester amplicon as a probe to detect said hypomethylation or said hypermethylation in a CNG triplet of DNA;
   wherein said master restriction enzyme cleaves a nonmethylated CNG DNA sequence but does not cleave a methylated CNG DNA sequence;
   wherein said partner restriction enzyme cleaves DNA to produce DNA fragments with a complexity of about 5% to about 25% of said genomic DNA in a size range which can be amplified by a DNA amplification enzyme; and
   wherein said driver DNA is cut with both the master restriction enzyme and the partner restriction enzyme, and then amplified by using primers that recognize DNA ends cut by said master restriction enzyme.

10. A method of isolating a probe to detect hypomethylation in a CNG triplet of DNA which comprises:
   a) cleaving a tester sample of genomic DNA with both a master restriction enzyme and a partner restriction enzyme to generate a cleaved tester sample;

b) ligating a first set of adaptors onto master enzyme cut DNA ends of said cleaved tester sample to generate a first-tester amplification template;

c) amplifying said first-tester amplification template to generate a first-tester amplicon by in vitro DNA amplification using primers that hybridize to said first set of adaptors;

d) cleaving off said first adaptors from said first-tester amplicon and ligating a second set of adaptors onto DNA ends of the first-tester amplicon to generate a second-adaptor-tester which has second adaptor ends;

e) melting and hybridizing the second-adaptor-tester with about a 10-fold to about a 10,000-fold molar excess of a driver DNA to generate a mixture of tester-tester product and tester-driver product;

f) adding nucleotides onto DNA ends present in said mixture to make a blunt-ended tester-tester product and a blunt-ended tester-driver product;

g) amplifying the blunt-ended tester-tester product and the blunt-ended tester-driver product by in vitro DNA amplification using primers that hybridize to second adaptor ends to generate a second-tester amplicon;

f) isolating a DNA fragment from said second tester amplicon as a probe to detect said hypomethylation or said hypermethylation in a CNG triplet of DNA;

wherein said master restriction enzyme cleaves a nonmethylated CNG DNA sequence but does not cleave a methylated CNG DNA sequence;

wherein said partner restriction enzyme cleaves DNA to produce DNA fragments with a complexity of about 5% to about 25% of said genomic DNA in a size range which can be amplified by a DNA amplification enzyme; and wherein said driver DNA is cut with both the master restriction enzyme and the partner restriction enzyme and amplified using primers that recognize DNA ends cut by said master restriction enzyme.

11. The method of claim 9 or 10 which further comprises digesting said blunt-ended tester-tester hybrid and said blunt-ended tester-driver hybrid with a nuclease to remove unhybridized regions in the blunt-ended tester-tester product and the blunt-ended tester-driver hybrid.

12. The method of claim 10 which further comprises cleaving off said second adaptors from said second-tester amplicon and ligating a third set of adaptors onto DNA ends of the second-tester amplicon to generate a third-adaptor-tester which has third-adaptor ends;

melting and hybridizing the third-adaptor-tester with about a 10-fold to about a 10,000-fold molar excess of a driver DNA to generate a second mixture of second tester-tester hybrid and second tester-driver hybrid;

adding nucleotides onto DNA ends present in said second mixture to make a second blunt-ended tester-tester hybrid and a second blunt-ended tester-driver hybrid;

amplifying the second blunt-ended tester-tester hybrid and the blunt-ended tester-driver hybrid by in vitro DNA amplification using primers that hybridize to third adaptor ends to generate a third-tester amplicon; and isolating a DNA fragment from said third tester amplicon as a probe to detect said hypomethylation in a CNG triplet of DNA.

13. The method of claim 9 or 10 wherein said master restriction enzyme is MspI, BsiSI or Hin2I.

14. The method of claim 9 or 10 wherein said partner restriction enzyme is MseI, Sau3A, RsaI, TspEI, MaeI, NiaIII or DpnI.

15. The method of claim 10 wherein said first set of adaptors cannot be ligated onto DNA ends cut by said partner enzyme.

16. The method of claim 10 wherein said second set of adaptors cannot be ligated onto DNA ends cut by said partner enzyme.

17. The method of claim 10 wherein said first set of adaptor oligonucleotides are selected from the group consisting of SEQ ID NO:1, SEQ ID NO:2, SEQ ID NO:3, SEQ ID NO:4, SEQ ID NO:5 and SEQ ID NO:6.

18. The method of claim 10 wherein said second set of adaptor oligonucleotides are selected from the group consisting of SEQ ID NO:1, SEQ ID NO:2, SEQ ID NO:3, SEQ ID NO:4, SEQ ID NO:5 and SEQ ID NO:6.

19. The method of claim 9 wherein said first tester amplicon is melted and hybridized with about a 10-fold to about a 10,000-fold molar excess of said driver DNA.

20. The method of claim 9 wherein said first tester amplicon is melted and hybridized with about a 10 to about a 1000-fold molar excess of a driver DNA.

21. The method of claim 9 wherein said first tester amplicon is melted and hybridized with about a 100-fold molar excess of a driver DNA.

22. The method of claim 10 wherein said second-adaptor-tester is melted and hybridized with about a 100-fold molar excess of a driver DNA.

23. The method of claim 9 or 10 wherein isolating said DNA fragment comprises cloning said DNA fragment into a vector.

24. The method of any one of claims 9 or 10 wherein said tester sample of genomic DNA is isolated from a sample of cancerous tissue.

25. The method of claim 24 wherein said cancerous tissue is isolated from a patient with Wilms' cancer, breast cancer, ovarian cancer, colon cancer, kidney cell cancer, liver cell cancer, lung cancer, leukemia, rhabdomyosarcoma, sarcoma, or hepatoblastoma.

26. The method of claim 9 or 10 wherein said tester sample of genomic DNA is isolated from a patient with a genetic defect in genomic imprinting.

27. The method of claim 9 or 10 wherein said driver DNA is genomic DNA isolated from normal cells of the same person as said tester DNA.

28. The method of claim 9 or 10 wherein said driver DNA is genomic DNA isolated from normal cells of the same tissue type as said tester sample of genomic DNA.

29. A method of detecting whether a CNG triplet of DNA is hypomethylated in a tester sample of genomic DNA which comprises:

a) cleaving a tester sample of genomic DNA with a master restriction enzyme and a partner restriction enzyme to generate a cleaved tester sample;

b) amplifying said cleaved tester sample by in vitro DNA amplification using primers that recognize DNA ends cut by said master restriction enzyme, to generate a first tester amplicon;

c) melting and hybridizing said first test amplicon with a driver DNA to generate a tester-tester hybrid and a tester-driver hybrid;

d) adding nucleotides to the ends of said tester-tester hybrid and said tester-driver hybrid to make a blunt-ended tester-tester hybrid and a blunt-ended tester-driver hybrid;

e) amplifying said blunt-ended tester-tester hybrid and said blunt-ended tester-driver hybrid by in vitro DNA amplification using primers which recognize only master-enzyme-cut DNA ends, to produce a second tester amplicon;

f) isolating a DNA fragment from said second tester amplicon;

j) preparing a probe from said DNA fragment;

g) isolating genomic DNA from a control tissue sample and a test tissue sample to generate a control-tissue DNA and a test-tissue DNA;

h) cleaving said control-tissue DNA and said test-tissue DNA with said master restriction enzyme to generate cleaved control-tissue DNA and cleaved test-tissue DNA;

i) hybridizing said probe to said cleaved control-tissue DNA and said cleaved test-tissue DNA to form a control-hydridization complex and a test-hybridization complex; and j) observing whether the size of the control-hydridization complex is the same as the size of the test-hybridization complex and thereby detecting hypomethylation in a CNG triplet of DNA which is present in a tester sample of genomic DNA;

wherein said master restriction enzyme cleaves a nonm-ethylated CNG DNA sequence but does not cleave a methylated CNG DNA sequence;

wherein said partner restriction enzyme cleaves DNA to produce DNA fragments with a complexity of about 5% to about 25% of said genomic DNA in a size range which can be amplified by a DNA amplification enzyme; and wherein said driver DNA is cut with both the master restriction enzyme and the partner restriction enzyme and amplified using primers that recognize DNA ends cut by said master restriction enzyme.

30. A method of detecting hypomethylation or hyperm-ethylation in a CNG triplet of DNA which is present in a test tissue sample which comprises:

a) cleaving a tester sample of genomic DNA with both a master restriction enzyme and a partner restriction enzyme to generate a cleaved tester sample;

b) ligating a first set of adaptors onto DNA ends of said cleaved tester sample to generate a first-tester amplification template;

c) amplifying said first-tester amplification template to generate a first-tester amplicon by in vitro DNA amplification using primers that hybridize to said first set of adaptors;

d) cleaving off said first adaptors from said first-tester amplicon and ligating a second set of adaptors onto DNA ends of the first-tester amplicon to generate a second-adaptor-tester which has second adaptor ends;

e) hybridizing the second-adaptor-tester with about a 10-fold to about a 10,000-fold molar excess of a driver DNA to generate a mixture of tester-tester hybrid and tester-driver hybrid;

f) adding nucleotides onto DNA ends present in said mixture to make a blunt-ended tester—tester hybrid and a blunt-ended tester-driver hybrid;

g) amplifying the blunt-ended tester—tester hybrid and the blunt-ended tester-driver hybrid by in vitro DNA amplification using primers that hybridize to second adaptor ends to generate a second-tester amplicon;

h) isolating a DNA fragment from said second-tester amplicon;

i) preparing a probe from said DNA fragment;

j) isolating genomic DNA from a control tissue sample and a test tissue sample to generate a control-tissue DNA and a test-tissue DNA;

k) cleaving said control-tissue DNA and said test-tissue DNA with said master restriction enzyme to generate cleaved control-tissue DNA and cleaved test-tissue DNA;

l) hybridizing said probe to said cleaved control-tissue DNA and said cleaved test-tissue DNA to form a control-hydridization complex and a test-hybridization complex; and n) observing whether the size of the control-hydridization complex is the same as the size of the test-hybridization complex;

wherein said master restriction enzyme cleaves a nonm-ethylated CNG DNA sequence but does not cleave a methylated CNG DNA sequence;

wherein said partner restriction enzyme cleaves DNA to produce DNA fragments with a complexity of about 5% to about 25% of said genomic DNA in a size range which can be amplified by a DNA amplification enzyme; and wherein said driver DNA is cut with both the master restriction enzyme and the partner restriction enzyme and amplified using primers that recognize DNA ends cut by said master restriction enzyme.

31. The method of claim 29 or 30 wherein said method is used for detecting cancer, cell-type specific expression, tissue-specific expression, or a genetic disease which alters methylation.

32. The method of claim 31 wherein said cancer is Wilms' cancer, breast cancer, ovarian cancer, colon cancer, kidney cell cancer, liver cell cancer, lung cancer, leukemia, rhabdomyosarcoma, sarcoma, or hepatoblastoma.

33. The method of claim 31 wherein said genetic disease which alters methylation is Beckwith-Wiedemann syndrome or Prader-Willi syndrome.

34. The method of claim 29 or 30 wherein said master restriction enzyme is MspI, BsiSI or Hin2I.

35. The method of claim 29 or 30 wherein said partner restriction enzyme is MseI, Sau3A, RsaI, TspEI, MaeI, NiaIII or DpnI.

36. The method of claim 30 wherein said first set of adaptors cannot be ligated onto DNA ends cut by said partner enzyme.

37. The method of claim 30 wherein said second set of adaptors cannot be ligated onto DNA ends cut by said partner enzyme.

38. The method of claim 30 wherein said first set of adaptors are selected from the group consisting of SEQ ID NO:1, SEQ ID NO:2, SEQ ID NO:3, SEQ ID NO:4, SEQ ID NO:5 and SEQ ID NO:6.

39. The method of claim 30 wherein said second set of adaptors is selected from the group consisting of SEQ ID NO:1, SEQ ID NO:2, SEQ ID NO:3, SEQ ID NO:4, SEQ ID NO:5 and SEQ ID NO:6.

40. The method of claim 29 wherein said first test amplicon is melted and hybridized with about a 10-fold to about a 10,000-fold molar excess of said driver DNA.

41. The method of claim 29 wherein said first test amplicon is melted and hybridized with about a 100-fold molar excess of said driver DNA.

42. The method of claim 29 wherein said blunt-ended tester—tester is hybridized with about a 10-fold to about a 10,000-fold molecular excess of said driver DNA.

43. The method of claim 29 wherein said blunt-ended tester—tester is hybridized with about a 100-fold molecular excess of said driver DNA.

44. The method of claim 29 or 30 wherein isolating said DNA fragment comprises cloning said DNA fragment into a vector.

45. The method of claim 29 or 30 wherein said driver DNA is genomic DNA isolated from normal cells of the same person as said tester DNA.

46. The method of claim 29 or 30 wherein said driver DNA is genomic DNA isolated from normal cells of the same tissue type as said tester sample of genomic DNA.

47. The method of claim 29 or 30 wherein observing whether the size of said control-hybridization complex is the same as the said size of the test-hybridization complex is done by Southern blot analysis.

48. The method of claim 29 or 30 which further comprises digesting said blunt-ended tester-tester hybrid and said blunt-ended tester-driver hybrid with a nuclease to remove unhybridized regions in the blunt-ended tester-tester product and the blunt-ended tester-driver hybrid.

49. A method of isolating a probe to detect hypermethylation in a CNG triplet of DNA which comprises:
   a) cleaving a normal sample of genomic DNA with a master restriction enzyme and a partner restriction enzyme to generate a cleaved normal sample;
   b) amplifying said cleaved normal sample using primers that recognize DNA ends cut by said master restriction enzyme, to generate a first normal amplicon;
   c) melting and hybridizing said first normal amplicon with a test driver DNA to generate a tester-tester hybrid and a normal-driver product;
   d) adding nucleotides to the ends of said tester-tester hybrid and said normal-driver product to make a blunt-ended tester-tester hybrid and a blunt-ended normal-driver product;
   e) amplifying said blunt-ended tester-tester hybrid and said blunt-ended normal-driver product by using primers which recognize only master-enzyme-cut DNA ends, to produce a second normal amplicon;
   f) isolating a DNA fragment from said second normal amplicon as a probe to detect said hypermethylation in a CNG triplet of DNA;
   wherein said master restriction enzyme cleaves a nonmethylated CNGDNA sequence but does not cleave a methylated CNGDNA sequence;
   wherein said partner restriction enzyme cleaves DNA to produce DNA fragments with a complexity of about 5% to about 25% of said genomic DNA in a size range which can be amplified by a DNA amplification enzyme; and
   wherein said test driver DNA is cut with both the master restriction enzyme and the partner restriction enzyme, and then amplified by using primers that recognize DNA ends cut by said master restriction enzyme.

50. A method of isolating a probe to detect hypermethylation in a CNG triplet of DNA which comprises:
   a) cleaving a normal sample of genomic DNA with a master restriction enzyme and a partner restriction enzyme to generate a cleaved normal sample;
   b) ligating a first set of adaptors onto master enzyme cut DNA ends of said cleaved normal sample to generate a first-normal amplification template;
   c) amplifying said first-normal amplification template to generate a first-normal amplicon by in vitro DNA amplification using primers that hybridize to said first set of adaptors;
   d) cleaving off said first adaptors from said first-normal amplicon and ligating a second set of adaptors onto DNA ends of the first-normal amplicon to generate a second-adaptor-normal DNA which has second adaptor ends;
   e) melting and hybridizing the second-adaptor-normal DNA with about a 10-fold to about a 10,000-fold molar excess of a test driver DNA to generate a mixture of tester—tester hybrid and normal-driver hybrid;
   f) adding nucleotides onto DNA ends present in said mixture to make a blunt-ended tester—tester hybrid and a blunt-ended normal-driver hybrid;
   g) amplifying the blunt-ended tester-tester hybrid and the blunt-ended normal-driver hybrid by in vitro DNA amplification using primers that hybridize to second adaptor ends to generate a second-normal amplicon;
   h) isolating a DNA fragment from said second-normal amplicon as a probe to detect hypermethylation in a CNG triplet of DNA;
   wherein said master restriction enzyme cleaves a nonmethylated CNG DNA sequence but does not cleave a methylated CNG DNA sequence;
   wherein said partner restriction enzyme cleaves DNA to produce DNA fragments with a complexity of about 5% to about 25% of said genomic DNA in a size range which can be amplified by a DNA amplification enzyme; and
   wherein said test driver DNA is cut with both the master restriction enzyme and the partner restriction enzyme, and then amplified by using primers that recognize DNA ends cut by said master restriction enzyme.

51. The method of claim 49 or 50 wherein said master restriction enzyme is MspI, BsiSI or Hin2I.

52. The method of claim 49 or 50 wherein said partner restriction enzyme is MseI, Sau3A, RsaI, TspEI, MaeI, NiaIII or DpnI.

53. The method of claim 50 wherein said first set of adaptors cannot be ligated onto DNA ends cut by said partner enzyme.

54. The method of claim 50 wherein said second set of adaptors cannot be ligated onto DNA ends cut by said partner enzyme.

55. The method of claim 49 wherein said first tester amplicon is melted and hybridized with about a 10-fold to about a 10,000-fold molar excess of said driver DNA.

56. The method of claim 49 wherein said first tester amplicon is melted and hybridized with about a 10 to about a 1000-fold molar excess of a driver DNA.

57. The method of claim 49 wherein said first tester amplicon is melted and hybridized with about a 100-fold molar excess of a driver DNA.

58. The method of claim 50 wherein said second-adaptor-tester is melted and hybridized with about a 100-fold molar excess of a driver DNA.

59. The method of claim 49 or 50 wherein isolating said DNA fragment comprises cloning said discrete DNA fragment into a vector.

60. The method of any one of claims 49 or 50 wherein said test driver DNA is isolated from a sample of cancerous tissue.

61. The method of claim 60 wherein said cancerous tissue is isolated from a patient with Wilms' cancer, breast cancer, ovarian cancer, colon cancer, kidney cell cancer, liver cell cancer, lung cancer, leukemia, rhabdomyosarcoma, sarcoma, or hepatoblastoma.

62. The method of claim 49 or 50 wherein said test driver DNA is isolated from a patient with a genetic defect in genomic imprinting.

63. The method of claim 49 or 50 wherein said normal sample of genomic DNA is isolated from normal cells of the same person as said test driver DNA.

64. The method of claim 49 or 50 wherein said normal sample of genomic DNA is isolated from normal cells of the same tissue as said test driver DNA.

65. A method of identifying a probe to detect a mutation in a tester sample of genomic DNA which comprises:

a) cleaving a tester sample of genomic DNA with both a master restriction enzyme and a detector restriction enzyme to generate a cleaved tester sample;

b) ligating a first set of adaptors onto master enzyme cut DNA ends of said cleaved tester sample to generate a first-tester amplification template;

c) amplifying said first-tester amplification template to generate a first-tester amplicon by in vitro DNA amplification using primers that hybridize to the first set of adaptors;

d) cleaving off the first adaptors from said first-tester amplicon and ligating a second set of adaptors onto DNA ends of said first-tester amplicon to generate a second-adaptor-tester which has second adaptor ends;

e) melting and hybridizing said second-adaptor-tester with about a 10-fold to about a 10,000-fold molar excess of a driver DNA to generate a mixture of tester-tester hybrid and tester-driver hybrid;

f) adding nucleotides onto DNA ends present in the mixture to make a blunt-ended tester-tester hybrid and a blunt-ended tester-driver hybrid;

g) amplifying said blunt-ended tester-tester hybrid and said blunt-ended tester-driver hybrid by in vitro DNA amplification using primers that hybridize to second adaptor ends to generate a second-tester amplicon;

h) isolating a DNA fragment from said second tester amplicon as a probe to detect a mutation in a tester sample of genomic DNA;

wherein the master restriction enzyme cleaves a nonmethylated CNG DNA sequence but does not cleave a methylated CNG DNA sequence;

wherein the detector restriction enzyme cleaves a normal DNA site but a mutant DNA site to produce DNA fragments with a complexity of about 5% to about 25% of the genomic DNA in a size range which can be amplified by a DNA amplification enzyme; and wherein the driver DNA is cut with both the master restriction enzyme and the detector restriction enzyme and amplified using primers that recognize DNA ends cut by the master restriction enzyme.

66. The method of claim 65 wherein said second-adaptor-tester is hybridized with about a 100-fold molecular excess of said driver DNA.

67. The method of claim 65 wherein isolating a DNA fragment comprises cloning said DNA fragment into a vector.

68. The method of claim 65 wherein said tester sample of genomic DNA is from a sample of cancerous tissue.

69. The method of claim 65 wherein said driver DNA is from a sample of non-tumorous tissue.

70. The method of claim 68 wherein said cancerous tissue is isolated from a patient with Wilms' cancer, breast cancer, ovarian cancer, colon cancer, kidney cell cancer, liver cell cancer, lung cancer, leukemia, rhabdomyosarcoma, sarcoma, or hepatoblastoma.

71. A method of detecting whether a DNA site is mutated in a genomic DNA present in a mammalian test sample of cells which includes:

a) isolating genomic DNA from a control sample of cells and a mammalian test sample of cells to generate a control-cell DNA and a test-cell DNA;

b) cleaving said control-cell DNA and the test-cell DNA with a detector restriction enzyme to generate cleaved control-cell DNA and cleaved test-cell DNA;

c) preparing a probe from a DNA isolated by the method of claim 65;

d) hybridizing said probe to said cleaved control-cell DNA and said cleaved test-cell DNA to form a control-hydridization complex and a test-hybridization complex; and e) observing whether the size of said control-hydridization complex is the same as the size of said test-hybridization complex;

wherein the detector restriction enzyme does not cleave a mutated DNA site but does cleave a corresponding nonmutated DNA site.

72. A probe isolated by the method of any one of claims 9, 10, 49, 50 or 65.

73. An isolated DNA of a size sufficient to ligate to DNA ends cut by a restriction enzyme and to act as a recognition site for primers during DNA amplification consisting essentially of SEQ ID NO:1, SEQ ID NO:2, SEQ ID NO:3, SEQ ID NO:4, SEQ ID NO:5, or SEQ ID NO:6.

74. A kit for detecting hypomethylation in a CNG triplet of DNA which is present in a mammalian test tissue sample which comprises a probe isolated by the method of any one of claims 9, 10, 49, 50 or 65.

75. A kit for detecting hypomethylation in a CNG triplet of DNA which is present in a test tissue sample which comprises a DNA selected from the group consisting of SEQ ID NO:7–10.

76. An isolated DNA which comprises SEQ ID NO:7, SEQ ID NO:8, SEQ ID NO:9, or SEQ ID NO:10.

77. The method of claim 1 or claim 71 wherein said genomic DNA contains viral DNA.

78. The method of claim 1 or claim 71 wherein said mammalian test sample contains viral DNA.

79. The method of claim 71 wherein said mutated DNA site is a point mutation, a deletion, an insertion, an amplification, or a rearrangement.

* * * * *